(12) United States Patent
Li et al.

(10) Patent No.: US 9,238,821 B2
(45) Date of Patent: Jan. 19, 2016

(54) METABOLIC ENGINEERING FOR PLANT DISEASE RESISTANCE

(75) Inventors: Wensheng Li, St. Louis, MO (US); Srinivasa Rao Uppalapati, Lone Grove, OK (US); Kirankumar S. Mysore, Ardmore, OK (US); Richard A. Dixon, Ardmore, OK (US); Lloyd W. Sumner, Ardmore, OK (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 911 days.

(21) Appl. No.: 12/760,440

(22) Filed: Apr. 14, 2010

(65) Prior Publication Data

US 2010/0319084 A1   Dec. 16, 2010

Related U.S. Application Data

(60) Provisional application No. 61/169,303, filed on Apr. 14, 2009.

(51) Int. Cl.

| | | |
|---|---|---|
| *C12N 15/82* | (2006.01) | |
| *C12N 9/02* | (2006.01) | |
| *A01N 65/20* | (2009.01) | |
| *A01N 65/00* | (2009.01) | |
| *A01N 65/08* | (2009.01) | |
| *A01N 65/38* | (2009.01) | |
| *C07K 14/415* | (2006.01) | |

(52) U.S. Cl.
CPC ............ *C12N 15/8282* (2013.01); *A01N 65/00* (2013.01); *A01N 65/08* (2013.01); *A01N 65/20* (2013.01); *A01N 65/38* (2013.01); *C07K 14/415* (2013.01); *C12N 9/0071* (2013.01); *C12N 9/0073* (2013.01); *C12N 15/8243* (2013.01); *C12N 15/825* (2013.01)

(58) Field of Classification Search
None
See application file for complete search history.

(56) References Cited

U.S. PATENT DOCUMENTS

| | | | |
|---|---|---|---|
| 6,072,103 A | 6/2000 | Wu et al. | |
| 6,878,859 B1 | 4/2005 | Dixon et al. | |
| 7,005,562 B2 | 2/2006 | Cade et al. | |
| 7,038,113 B1 | 5/2006 | Dixon et al. | |
| 7,084,265 B1* | 8/2006 | Ayabe et al. | 536/23.6 |
| 7,173,166 B2 | 2/2007 | Vijaybhaskar et al. | |
| 7,442,851 B2 | 10/2008 | Dixon et al. | |
| 7,667,094 B2 | 2/2010 | Yoshioka | |
| 7,750,211 B2 | 7/2010 | Dixon et al. | |
| 7,816,507 B2 | 10/2010 | Tian et al. | |
| 8,138,392 B2* | 3/2012 | Uppalapati et al. | 800/285 |
| 2004/0128711 A1 | 7/2004 | Dixon et al. | |
| 2004/0248303 A1 | 12/2004 | Cade et al. | |
| 2005/0172354 A1 | 8/2005 | Dixon et al. | |
| 2005/0257286 A1 | 11/2005 | Vijaybhaskar et al. | |
| 2006/0053509 A1 | 3/2006 | Yoshioka | |
| 2008/0282423 A1 | 11/2008 | Tian et al. | |
| 2008/0317880 A1 | 12/2008 | Broeckling et al. | |
| 2010/0017913 A1 | 1/2010 | Uppalapati et al. | |

OTHER PUBLICATIONS

Akashi et al. (1999) Plant Physiology 121:821-828.*
Uppalapati et al. (2009) MPMI 22(Jan. 1): 7-17.*
La Camera et al. (2004) Immunological Reviews 198: 267-284.*
Deavours and Dixon (2005) Plant Physiology 138 (August):2245-2259.*
Bourdon et al. (2002) Plant Science 163:297-305.*
Akashi of al., "Cloning and functional expression of a cytochrome P450 cDNA encoding 2-hydroxyisoflavanone synthase involved in biosynthesis of the isoflavonoid skeleton in licorice," *Plant Physiol.*, 121:821-828, 1999.
Blount et al., "Stress responses in alfalfa (*Medicago sativa* L.) XVI. Antifungal activity of medicarpin and its biosynthetic precursors; implications for the genetic manipulation of stress metabolites," *Physiol. Mol. Plant Path.*, 41(5):333-349, 1992.
Dixon et al., "The phenylpropanoid pathway and plant defence—a genomics perspective," *Mol. Plant Path.*, 3(5):371-390, 2002.
Dixon, "Natural products and plant disease resistance," *Nature*, 411:843-847, 2001.
Farag et al., "Metabolic profiling and systematic identification of flavonoids and isoflavonoids in roots and cell suspension cultures of medicago truncatula using HPLC-UV-ESI-MS and GC-MS," *Phytochemistry*. 68:342-354, 2007.
Farag et al., "Metabolomics reveals novel pathways, differential and elicitor-specific responses in phenylpropanoid and isoflavonoid biosynthesis in medicago truncatula cell cultures." *Plant Physiol.*, 146(2):387-402. 2008.
GenBank Accession No. AB023636, dated Apr. 21, 2000.
GenBank Accession No. AY167424, dated Jan. 7, 2003.
GenBank Accession No. DQ335809, dated Jun. 6, 2007.
GenBank Accession No. DQ354373, dated Jul. 1, 2006.
GenBank Accession No. EU526033, dated Jan. 29, 2009.
GenBank Accession No. EU526034, dated Jan. 29, 2009.
GenBank Accession No. EU526035, dated Jan. 29, 2009.
GenBank Accession No. EU526036, dated Jan. 29, 2009.
Gomez et al., "Medicago truncatula and glomus intraradices gene expression in cortical cells harboring arbuscules in the arbuscular mycorrhizal symbiosis," *BMC Plant Bio.*, 9(10), DOI:10.1186/1471-2229-9-10, 2009.
Harrison et al., "A phsphate transporter from medicago truncatula involved in the acquisition of phosphate released by arbuscular mycorrhizal fungi," *Plant Cell*, 14:2413-2429, 2002.
Harrison et al., "Signaling the arbuscular mycorrhizal symbiosis," *Ann. Rev. of Microbiol.*, 59:19-42, 2005.

(Continued)

*Primary Examiner* — Steven Bernacki
(74) *Attorney, Agent, or Firm* — Dentons US LLP

(57) ABSTRACT

The invention provides methods and compositions for making a dicotyledonous plant that is susceptible to *Phymatotrichopsis* Root Rot (PRR) more resistant to PRR, by metabolic engineering of the plant's flavonoid and isoflavonoid biosynthetic pathways. Thus, methods for increasing the synthesis and accumulation of medicarpin and/or 7,4'-dihydroxyflavone in plants such as alfalfa are provided.

24 Claims, 11 Drawing Sheets

(56) References Cited

OTHER PUBLICATIONS

Kakar et al., "A community resource for high-throughput quantitative RT-PCR analysis of transcription factor gene expression in medicago truncatula," *Plant Methods*, 4:18, 2008.

Kessmann et al., "Stress responses in alfalfa (*Medicago sativa* L.) V. Constitutive and elicitor-induced accumulation of isoflavonoid conjugates in cell suspension cultures," *Plant Physiol.*, 94:227-232. 1990.

Li et al., "Metabolomics reveals unique medicago truncatula responses to the devastating phymatotrichopsis omnivora root rot pathogen and strategies for metabolic engineering of resistance," 57$^{th}$ Amer. Soc. for Mass Spectrometry Meeting, Philadelphia, PA, May 31-Jun. 4, 2009.

Martens et al., "Flavones and flavone synthases," *Phytochemistry*, 66:2399-2407, 2005.

Naoumkina et al., "Elicitor-induced transcription factors for metabolic reprogramming of secondary metabolism in medicago truncatula," *BMC Plant Biol.*, 8:132, 2008.

Pontier et al., "hsr203J, a tobacco gene whose activation is rapid, highly localized and specific for incompatible plant/pathogen interactions," *Plant J.*, 5:507-521, 1994.

Saunders at al., "The characterization of defense responses to fungal infection in alfalfa," *Biocontrol*, 49:715-728, 2005.

Schliemann et al., "Metabolite profiling of mycorrhizal roots of medicago truncatula," *Phytochemistry*, 69:112-146, 2008.

Sumner et al., "Plant metabolomics: large-scales phytochemistry in the functional genomics era," *Phytochemistry*, 62:817-836, 2003.

Suzuki et al., "Methyl jasmonate and yeast elicitor induce differential transcriptional and metabolic re-programming in cell suspension cultures of the model legume medicago truncatula." *Planta*, 220:696-707. 2005.

Weber et al., "Divinyl ether fatty acid synthesis in late blight—diseased potato leaves," *Plant Cell*, 11:485-494, 1999.

Yamamoto et al., "Characterization of cis-acting sequences regulating root-specific gene expression in tobacco," *Plant Cell*, 3:371-382, 1991.

Zhang et al., "Flavone synthases from medicago truncatula are flavanone-2-hydroxylases and are important for nodulation," *Plant Physiol.*, 144:741-751, 2007.

Zhang et al., "Flavones and flavonols play distinct critical roles during nodulation of medicago truncatula by sinorhizobium meliloti," *Plant J.*, 57:171-183, 2009.

\* cited by examiner

This visualization shows records in a dendrogram (a tree graph) based on the similarity between them Calculation settings:
------------------------------------

Colors:
0R_ratio
Colored by Default
1                             1

1R_ratio
Colored by Default
0.2311209264016    3.96553409754

3R_ratio
Colored by Default
0.4763150657989    14.11094260549

5R_ratio
Colored by Default
0.082313810874...  9.599999717005

7R_ratio
Colored by Default
0.026353361996...  24.10764562803

9R_ratio
Colored by Default
0.017064856917...  27.6649323333

Order by Hierarchical Clustering (order

METABOLIC ENGINEERING FOR PLANT DISEASE RESISTANCE

CROSS-REFERENCE TO RELATED APPLICATIONS

This application claims the benefit of priority of U.S. Provisional Application Ser. No. 61/169,303, filed on Apr. 14, 2009, the disclosure of which is incorporated herein by reference in its entirety.

INCORPORATION BY REFERENCE OF SEQUENCE LISTING IN COMPUTER READABLE FORM

The Sequence Listing, which is a part of the present disclosure, includes a computer readable form 36.7 kb file entitled "NBLE066US_ST25.TXT" comprising nucleotide and/or amino acid sequences of the present invention submitted via EFS-Web. The subject matter of the Sequence Listing is incorporated herein by reference in its entirety.

BACKGROUND OF THE INVENTION

1. Field of the Invention

The present invention generally relates to plant genetics. More specifically, the invention relates to compositions conferring resistance to plant disease, and methods for use thereof.

2. Description of the Related Art

Cotton Root Rot, also known as *Phymatotrichopsis* Root Rot (PRR) is one of most destructive diseases of legumes such as alfalfa. It is caused by an asexual soil-borne fungus, *Phymatotrichopsis omnivora* (Duggar) previously known as *Phymatotrichum omnivorum*, and causes significant economic losses every year in the United States. *P. omnivora* has a very broad host range and attacks almost 2,000 dicotyledonous species, but interestingly it does not cause disease on monocotyledonous plant species, including maize and sorghum. The disease is economically important in alfalfa, other legumes such as beans and peanut, cotton, sweet potatoes, ornamental shrubs, and fruit, nut, and shade trees (Lyda, 1978; Lyda and Kenerly, 1992; Streets and Bloss, 1973).

SUMMARY OF THE INVENTION

The invention provides, in one aspect, a transgenic dicotyledonous plant comprising a heterologous nucleic acid sequence that increases expression of flavone synthase or isoflavone synthase, wherein synthesis of medicarpin and/or 7,4'-dihydroxyflavone is up-regulated in the plant. In certain embodiments, the heterologous nucleic acid sequence encodes flavone synthase or isoflavone synthase, or a transcriptional regulatory factor that up-regulates expression of flavone synthase or isoflavone synthase. In some embodiments, the sequence encoding flavone synthase or isoflavone synthase, or a transcriptional regulatory factor that up-regulates expression of flavone synthase or isoflavone synthase, is operably linked to a constitutive promoter. In a particular embodiment, the constitutive promoter is a CaMV 35S promoter. In other embodiments, the heterologous nucleic acid sequence encoding flavone synthase or isoflavone synthase or a transcriptional regulatory factor that up-regulates expression of flavone synthase or isoflavone synthase is operably linked to an inducible promoter. In some embodiments, expression of the heterologous nucleic acid sequence is inducibly up-regulated in response to infection by a fungal plant pathogen or a fungal mutualist. In particular embodiments, a plant of the invention comprises a heterologous nucleic acid sequence wherein the fungal-inducible promoter is an hsr203J promoter, a PVS3 promoter, a NI16 promoter, a MtPT4 promoter, or an STS8 stilbene synthase promoter.

In certain embodiments, the fungal plant pathogen is *Phymatotrichopsis omnivora*. Thus, in some embodiments, the plant exhibits increased resistance to *Phymatotrichopsis omnivora* relative to an otherwise identical plant not comprising the heterologous nucleic acid sequence. In certain embodiments the plant is a legume. In particular embodiments, the plant is a *Medicago* sp. plant, such as alfalfa.

In some embodiments, the heterologous nucleic acid sequence is expressed in root tissue. Thus, in particular embodiments, the heterologous nucleic acid sequence is operably linked to a root-preferred promoter. In even more particular embodiments the root-preferred promoter is an RB7, RPE15, RPE14, RPE19, RPE29, RPE60, RPE2, RPE39, RPE61, SHR, ELG3, EXP7, EXP18 or Atlg73160 promoter.

In some embodiments, the plant accumulates about 10-100 µM 7,4-dihydroxyflavone and/or medicarpin. In certain embodiments the accumulation of 7,4-dihydroxyflavone and/or medicarpin occurs prior to the plant's contact with *Phymatotrichopsis omnivora*. In other embodiments the accumulation of 7,4-dihydroxyflavone and/or medicarpin occurs subsequent to the plant's contact with *Phymatotrichopsis omnivora*.

In another aspect of the invention, there is provided seed comprising the heterologous nucleic acid sequence that increases expression of flavone synthase or isoflavone synthase, wherein synthesis of medicarpin and/or 7,4'-dihydroxyflavone is up-regulated in a plant grown from the seed. Yet another aspect of the invention provides a plant cell comprising the heterologous nucleic acid sequence.

The invention also provides, in another aspect, a method of producing a dicotyledonous plant variety with increased resistance to *Phymatotrichopsis omnivora*, the method comprising: expressing in the plant variety a heterologous nucleic acid sequence encoding flavone synthase, isoflavone synthase, or a regulatory transcription factor that increases accumulation of medicarpin and/or 7,4'-dihydroxyflavone in the plant, relative to an otherwise similar plant not comprising the heterologous nucleic acid sequence. In some embodiments of such a method, the heterologous nucleic acid sequence encoding flavone synthase or isoflavone synthase is operably linked to a constitutive promoter. In particular embodiments of the method, the constitutive promoter is a CaMV 35S promoter. Alternatively, in other embodiments, the heterologous nucleic acid sequence encoding flavone synthase or isoflavone synthase is operably linked to an inducible promoter. In certain embodiments the heterologous nucleic acid sequence encodes a transcriptional regulatory factor.

In some embodiments of the method, expression of the heterologous nucleic acid sequence is inducibly up-regulated in response to infection by a fungal plant pathogen or a fungal mutualist. In particular embodiments, the fungal pathogen-inducible promoter is an hsr203J promoter, a PVS3 promoter, a NI16 promoter, a MtPT4 promoter, or a STS8 stilbene synthase promoter. In particular embodiments of the method, the fungal plant pathogen is *Phymatotrichopsis omnivora*.

In other embodiments of the method, the heterologous nucleic acid sequence is transformed into a plant of the variety, and progeny of the plant are grown such that a modified variety of the plant is produced that is homozygous for the heterologous nucleic acid sequence. In certain embodiments, the plant is alfalfa, bean, peanut, cotton, sweet potato, or a woody plant. In particular embodiments of the method, the plant is a *Medicago* sp. plant, such as an alfalfa plant.

In another aspect, the invention provides a method of obtaining a plant of a dicotyledonous plant variety that is naturally susceptible to *Phymatotrichopsis* Root Rot in soil that comprises *Phymatotrichopsis omnivora*, the method comprising: (a) expressing one or more heterologous nucleic acid sequence(s) in the plant variety that up-regulates the synthesis of medicarpin or 7,4'-dihydroxyflavone in the plant variety, and (b) selecting a plant expressing the heterologous nucleic acid sequence. The method further comprises, in certain embodiments, the step of (c) analyzing the plant for infection by *P. omnivora*. In some embodiments of the invention, the heterologous nucleic acid sequence is transformed into a plant of the variety and progeny of the plant are grown such that a modified variety of the plant is produced that is homozygous for the heterologous nucleic acid sequence. In certain embodiments the heterologous nucleic acid sequence is constitutively expressed in the plant. In yet other embodiments the heterologous nucleic acid sequence is expressed in the roots of the plant.

In some embodiments the heterologous nucleic acid sequence is expressed in response to infection by a root-infecting fungal plant pathogen or a fungal mutualist. The plant is, in certain embodiments, a cotton, alfalfa, bean, peanut, sweet potato, or woody plant. In particular embodiments the plant is a *Medicago* sp. plant. In even more particular embodiments, the plant is an alfalfa plant.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

BRIEF DESCRIPTION OF THE SEQUENCES

SEQ ID NO:1 *Glycyrrhiza echinata* CYP93C2 Isoflavone Synthase (IFS) DNA sequence.
SEQ ID NO:2 *Glycyrrhiza echinata* CYP93C2 Isoflavone Synthase (IFS) amino acid sequence.
SEQ ID NO:3 *M. truncatula* CYP93C19 IFS nucleotide sequence.
SEQ ID NO:4 *M. truncatula* CYP93C19 IFS amino acid sequence.
SEQ ID NO:5 *M. truncatula* Flavone Synthase CYP93B10 amino acid sequence.
SEQ ID NO:6 *M. truncatula* Flavone Synthase CYP93B11 nucleotide sequence.
SEQ ID NO:7 *M. truncatula* Flavone Synthase CYP93B11 amino acid sequence.
SEQ ID NO:8 *M. truncatula* CYP93B12 Flavone Synthase nucleotide sequence (Li et al., 2007).
SEQ ID NO:9 *M. truncatula* CYP93B12 Flavone Synthase amino acid sequence.
SEQ ID NO:10 WRKY Transcription Factor W100577 DNA sequence from *M. truncatula*.
SEQ ID NO:11 WRKY Transcription Factor W100577 amino acid sequence from *M. truncatula*.
SEQ ID NOs:12-23 PCR primers.

DETAILED DESCRIPTION OF THE INVENTION

The invention relates, in one aspect, to the surprising discovery that plants, such as alfalfa, may be engineered to over express certain flavonoid and isoflavonoid phytoalexins such as medicarpin and/or 7,4'-dihydroxyflavone, to exhibit enhanced resistance to *Phymatotrichopsis omnivora*, the causal agent of Cotton Root Rot. This discovery is unexpected because metabolomic profiling of a plant's response in its interaction with *P. omnivora* had not previously been performed. Thus, the invention overcomes limitations in the art by providing plants engineered to be resistant to Cotton Root Rot, and also provides methods for producing plants with enhanced resistance to *P. omnivora*. Plants that are provided include transgenic dicotyledonous plants, such as alfalfa, comprising heterologous DNA sequences that lead to overexpression of isoflavone synthase (IFS), flavone synthase (FS), and/or related flavonoid or isoflavonoid biosynthetic enzymes or regulatory transcription factor(s), for instance under the control of a constitutive, root-preferred, or inducible promoter, in order to achieve elevated accumulation of one or more phytoalexin(s) that inhibit growth of *P. omnivora*. Such phytoalexins may include, for instance, medicarpin and 7,4'-dihydroxyflavone. Thus, in particular embodiments, plants of the invention comprise an elevated level of medicarpin or 7,4'-dihydroxyflavone as compared to otherwise identical plants that do not comprise a heterologous DNA sequence that leads to over expression of isoflavone synthase (IFS), flavone synthase (FS), and/or related flavonoid or isoflavonoid biosynthetic enzymes or regulatory transcription factor(s).

Figure 1:
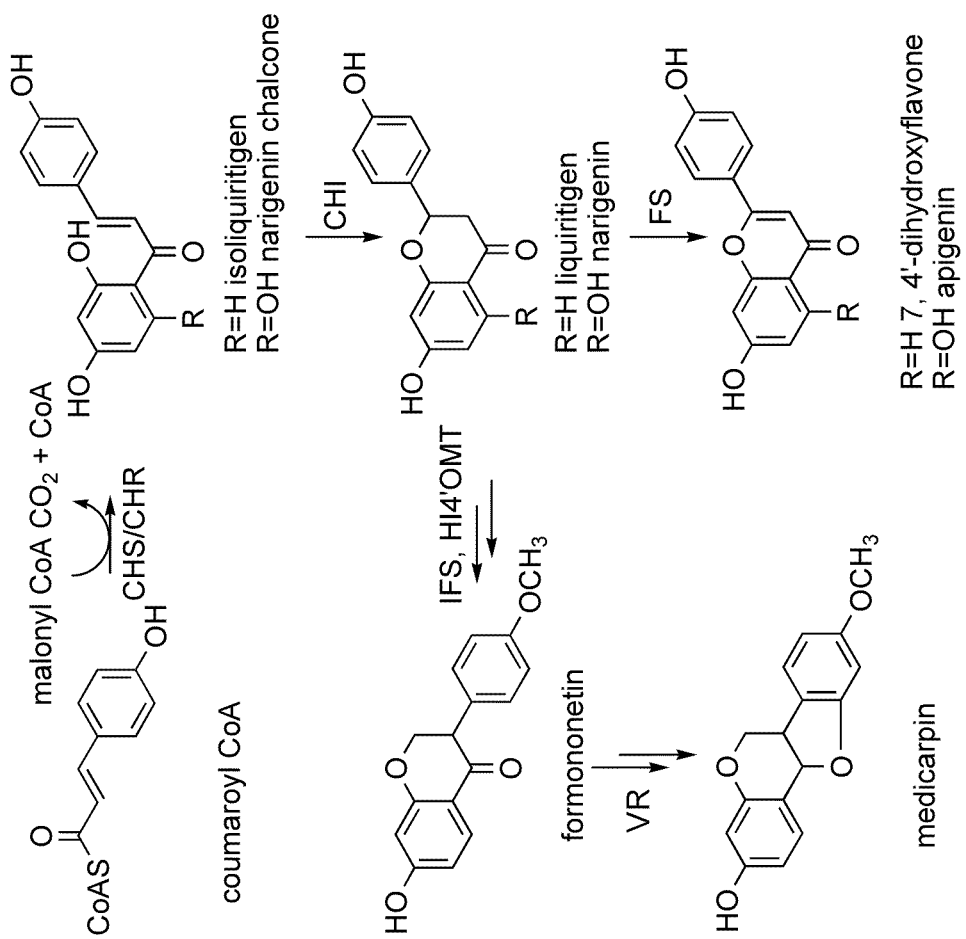
FIG. 1. Schematic illustration of the biosynthetic pathways leading to flavonoid and isoflavonoid natural products. CHS, chalcone synthase; CHR, chalcone reductase; CHI, Chalcone isomerase; FS, flavone synthase; IFS, 2-hydroxyisoflavanone synthase; HI4'OMT, 7,4'-hydroxyisoflavanone 4'-O-methyltransferase, VR, vestitone reductase.

Metabolite profiling was employed to analyze metabolites accumulated in *M. truncatula* root upon *P. omnivora* infection. For the first time, a pathogenic fungus is reported to suppress isoflavonoid biosynthesis in *Medicago* to enable pathogenesis. A biosynthetic scheme for production of flavonoid and isoflavonoid compounds such as medicarpin and 7,4'-dihydroxyflavone is shown in FIG. 1. As a direct result of redirected metabolic flux or as an alternate defense mechanism, activity of *Medicago* flavonoid synthase increased, as well as levels of related dihydroxy and trihydroxy flavones. The flavone 7, 4'-dihydroxyflavone and the isoflavone medicarpin were demonstrated to have substantial in vitro growth inhibitory activity against *P. omnivora*, providing a strategy for metabolic engineering of *Medicago* resistance to *P. omnivora* via over-expression of flavonoid and/or isoflavonoid synthesis-related genes and elevated accumulation of compounds that inhibit growth of *P. omnivora*.

Plants have developed various defense mechanisms in response to fungal infection. In legumes, flavonoids and isoflavonoids serve as signal molecules to promote colonization by symbiotic bacteria (Zhang et al., 2009) or arbuscular mycorrhizal fungi (Harrison, 2005), or as potent phytoanticipins or phytoalexins (Dixon, 2001; Dixon et al., 2002). The major phytoalexins in legumes such as *Medicago* sp. are believed to be pterocarpans which are isoflavonoid derivatives and are synthesized upon pathogenic fungal infection. The pterocarpans maackiain and pisatin are the primary phytoalexins in peanut, and medicarpin is the predominant phytoalexin in *Medicago*. Increased accumulation of medicarpin has been observed in alfalfa root when infected by the pathogenic fungus *Colletotrichum trifolii* (Saunders and O'Neil, 2005), and in *Medicago truncatula* cell cultures when exposed to a yeast extract (Suzuki et al., 2005; Farag et al., 2007; Farag et al., 2008).

Figure 2:
FIG. 2. *M. truncatula* was successfully infected by *P. omnivora*. The pair of plants in the left panel are from 5 days post inoculation ("DPI") and the plants in the right panel are from 11 DPI. In each panel, the plant on the left is an infected plant and the plant on the right is a control plant. Necrosis was visible at 5 DPI and progressed. At 11 DPI plants were severely necrotic and collapsed shortly after 11 DPI.
Figure 2:
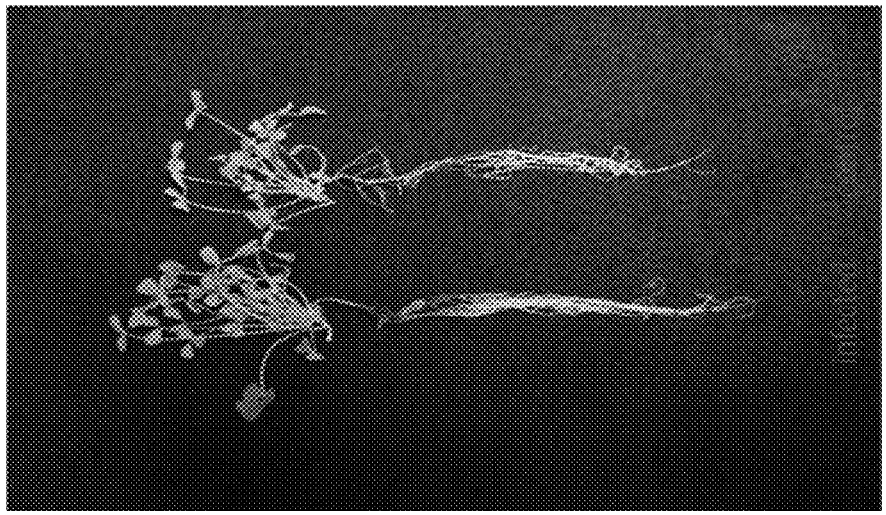
Figure 3:
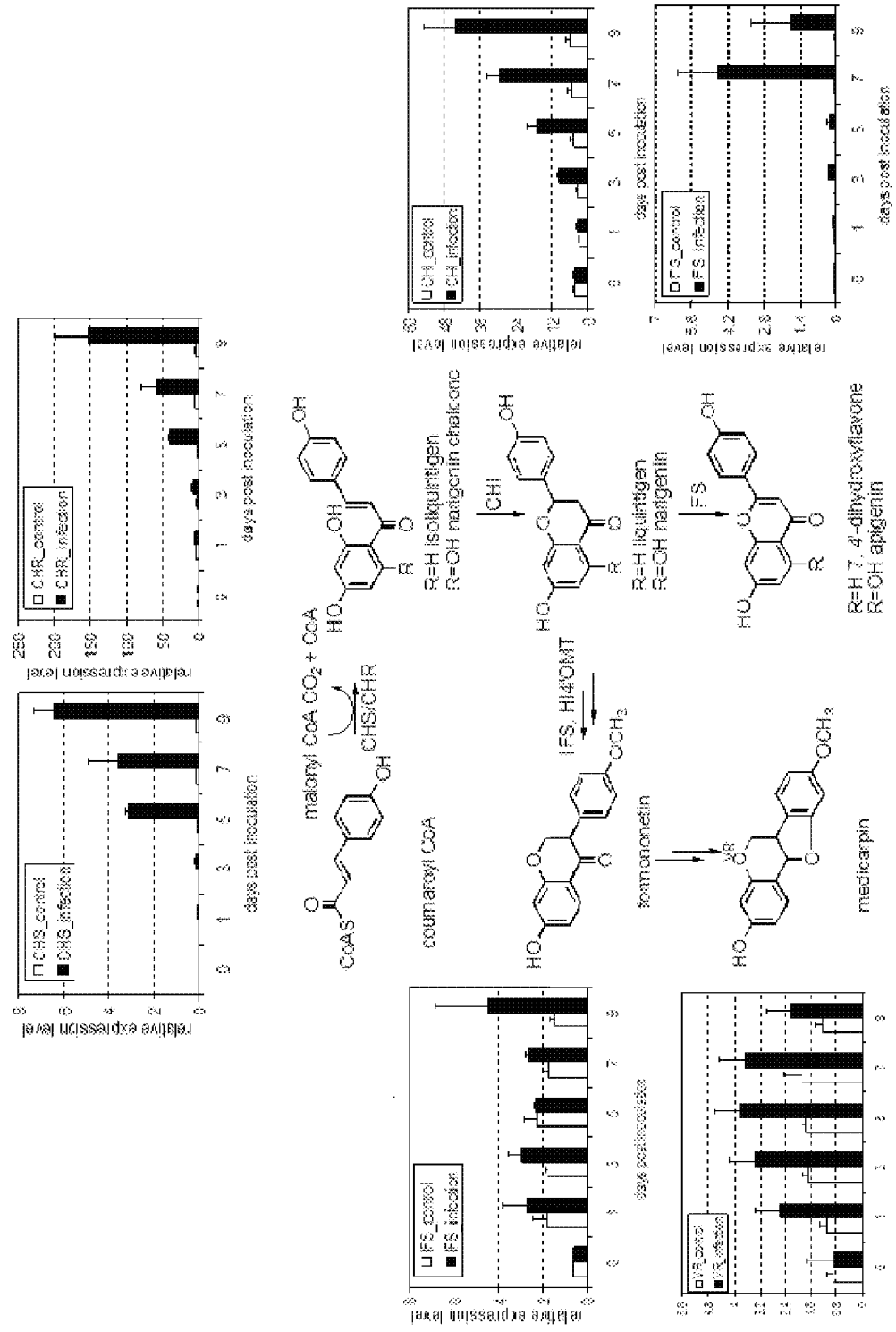
FIG. 3. Quantitative RT-PCR of flavonoid and isoflavonoid biosynthetic genes. RNA was isolated from root of *M. truncatula* plant grown in growth chamber conditions and harvested at 0, 1, 3, 5, 7, 9 days post infection with *P. omnivora*. All data were quantified relative to ubiquitin as a reference and represent the mean of 3 replicates. Control samples are represented by open bars and *P. omnivora* infected plant samples by solid bars.

The ability of *P. omnivora* to infect the model legume *M. truncatula* was confirmed (FIG. 2). Analysis indicated that medicarpin levels decreased in *Medicago truncatula* following infection with *P. omnivora*. This is contrary to the typical defense response, and the pathogenic fungus *P. omnivora* appears to be suppressing medicarpin accumulation to circumvent a plant defense mechanism. To determine if the isoflavonoid pathway was being suppressed at the molecular level, qRT-PCR (quantitative real time polymerase chain reaction) of isoflavone pathway genes was performed. Isoflavonoid biosynthetic genes such as isoflavone synthase were only marginally increased relative to early pathway genes such as chalcone synthase and chalcone isomerase (FIG. 3). These data indicate that *P. omnivora* may successfully infect plants by circumventing isoflavonoid phytoalexin biosynthesis at the molecular level.

In contrast to the effect of *P. omnivora* infection on isoflavonoid synthesis, flavones and the common flavone precursors accumulated at much higher levels in the root of *M. truncatula* (FIG. 4) upon *P. omnivora* infection. Quantitative RT-PCR data show that flavone synthase (e.g. Zhang et al., 2007; Martens and Mithofer, 2005), which is responsible for the biosynthesis of the flavones apigenin and 7,4'-dihydroxyflavone, was up-regulated more than 80 fold. Thus the down regulation of the isoflavone pathway apparently disrupts the phenylpropanoid network and redirects flux towards flavone biosynthesis. The induction of specific flavonoids and the redistribution of metabolic flux could also represent an alternate plant defense mechanism. Thus various isoflavonoids and flavonoids observed during the *Medicago-P. omnivora* interaction were tested for antimicrobial activity against *P. omnivora*. The trihydroxyflavone apigenin was substantially induced during infection, but was not in vitro active against *P. omnivora*. However, both medicarpin and 7,4'-dihydroxyflavone possessed substantial in vitro growth inhibitory activity against *P. omnivora* (e.g. FIG. 5).

Thus, since both of these are active as phytoalexins against *P. omnivora*, enhanced and timely synthesis of these compounds will serve to increase a plant's resistance to *P. omnivora*. That is, in certain embodiments of the invention, over-expression of isoflavone synthase, flavone synthase, or a related regulatory transcription factor under a constitutive, root-specific, or chemically- or pathogen-inducible, promoter would lead to sufficient accumulation of these endogenous antimicrobial compounds to enhance host plant resistance to *P. omnivora*. Sequences of isoflavone synthase, flavone synthase, and transcription factors active in regulating isoflavonoid and flavonoid biosynthesis from *Medicago* and other plants are known (e.g. Naoumkina et al., 2008; Zhang et al., 2007; Akashi et al, 1999; Gomez et al. 2009; GenBank Accessions EU526033, EU526034, EU526035, EU526036, AB023636; DQ354373; DQ335809; AY167424) and may be utilized in the creation of transgenic plants with enhanced levels of phytoalexins that inhibit growth of *P. omnivora*.

In one embodiment, a plant provided by the invention is more resistant to Cotton Root Rot than an otherwise similar plant not comprising a recombinant DNA construct that allows for an increase in the level of medicarpin and/or 7,4'-dihydroxyflavone. A first plant can be considered more resistant to Cotton Root Rot than a second plant when the first plant exhibits less disease, or the disease progresses more slowly in the first plant than in the second plant. The amount of disease infecting a plant can be measured by any means known in the art. As shown in Example 4 and FIG. 2, roots of inoculated rooted cuttings or seedlings can be observed after a particular time interval or intervals, and percentage of roots that are discolored can be estimated. Loss of foliage, necrosis, wilting, or other symptoms can also be measured.

Such embodiments are not limited to a particular plant; any dicotyledonous plant that is a host of *P. omnivora* could be made more resistant to Cotton Root Rot using these methods. Included are plants grown for food, feed, fuel or fiber, ornamental plants, and wild plants. In some embodiments, the plant is cotton, alfalfa, bean, peanut, sweet potato, or a woody plant. In specific embodiments, the plant is alfalfa.

Plants of these embodiments produce increased amounts of certain flavonoids and isoflavonoids such as 7,4'-dihydroxyflavone or medicarpin (which inhibit growth of *P. omnivora*; e.g. FIG. 5), naringenin, and apigenin, and may also be engineered to produce increased levels of an isoflavonoid, such as medicarpin which inhibits the growth of *P. omnivora*. Thus, in one aspect of the invention, phenylpropanoid metabolism is altered to direct flux towards synthesis of medicarpin and/or 7,4'-dihydroxyflavone, to result in increased production of phytoalexins, including 7,4-dihydroxyflavone, which are toxic to a fungal pathogen such as *P. omnivora*. In particular embodiments, the root-infecting fungal plant pathogen is *Phymatotrichopsis omnivora*.

I. Application of the Invention

As indicated above, one application of the invention is to provide methods to increase the resistance of a plant to *P.*

*omnivora*. Modulation of the phenotype of a plant or plant tissue may be obtained in accordance with the invention by introduction of recombinant nucleic acid sequences that result in increased, e.g. constitutive, synthesis of medicarpin and/or 7,4'-dihydroxyflavone. Such sequences may be identical to or display, for example, at least 75%, 80%, 85%, 90%, 95%, 98%, or 99% sequence similarity with, for instance, SEQ ID NO:1, SEQ ID NO:3, or SEQ ID NO:10, and possess flavone synthase activity, isoflavone synthase activity, or activity in transcriptional regulation of genes of the flavonoid or isoflavonoid biosynthetic pathways. As used herein, "hybridization" or "hybridizes" is understood to mean the forming of a double or triple stranded molecule or a molecule with partial double or triple stranded nature. As used herein "stringent condition(s)" or "high stringency" are those conditions that allow hybridization between or within one or more nucleic acid strand(s) containing complementary sequence(s), but precludes hybridization of random sequences.

Stringent conditions tolerate little mismatch between a nucleic acid and a target strand. Such conditions are well known to those of ordinary skill in the art, and are preferred for applications requiring high selectivity. Medium stringent conditions may comprise relatively low salt and/or relatively high temperature conditions, such as provided by about 1×SSC, and 65° C. High stringency may be defined as 0.02M to 0.10M NaCl and 50° C. to 70° C. Specific examples of such conditions include 0.02M NaCl and 50° C.; 0.02M NaCl and 60° C.; and 0.02M NaCl and 70° C.

Alterations of the native amino acid sequence to produce variant polypeptides can be prepared by a variety of means known to those ordinarily skilled in the art. For instance, amino acid substitutions can be conveniently introduced into the polypeptides by changing the sequence of the nucleic acid molecule at the time of synthesis. Site-specific mutations can also be introduced by ligating into an expression vector a synthesized oligonucleotide comprising the modified sequence. Alternately, oligonucleotide-directed, site-specific mutagenesis procedures can be used, such as disclosed in Walder et al. (1986); and U.S. Pat. Nos. 4,518,584 and 4,737,462.

In making such changes, the hydropathic index of amino acids may be considered. The importance of the hydropathic amino acid index in conferring interactive biological function on a protein is generally understood in the art (e.g. Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid may be assigned a hydropathic index on the basis of their hydrophobicity and charge characteristics. These are, for instance: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those skilled in the art and include: arginine and lysine; glutamate and aspartate; serine and threonine; glutamine and asparagine; and valine, leucine, and isoleucine.

It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture. It is also understood that compositions and conditions for hybridization are mentioned by way of non-limiting examples only, and that the desired stringency for a particular hybridization reaction in a plant cell is often determined empirically by comparison to one or more positive or negative controls. Depending on the application envisioned it is preferred to employ varying conditions of hybridization to achieve varying degrees of selectivity of a nucleic acid towards a target sequence. Thus, recombinant DNA constructs comprising nucleotide sequences displaying 90%, 95%, 98%, 99%, or greater similarity over the length of their coding regions and that encode a functional FS, IFS, or flavonoid biosynthesis transcriptional regulatory activity (e.g. CYP93B10, CYP93B11, CYP93B12, CYP93C2, CYP93C19, or the 100577 "WRKY" regulatory transcription factor protein; e.g. SEQ ID NOs:2, 4, 5, 7, 9, or 11) may be utilized in the present invention. The coding sequences of such genes may be operably linked to and under transcriptional control of a constitutive, root-preferred, and/or inducible promoter as outlined below.

II. Plant Transformation Constructs

Certain embodiments of the current invention concern plant transformation constructs. For example, one aspect of the current invention is a plant transformation vector comprising a nucleotide sequence that encodes a polypeptide with FS or IFS activity, or a transcriptional regulatory factor that up-regulates FS and/or IFS activity. Such coding sequences may be present in one or more plant expression cassettes and/or transformation vectors for introduction to a plant cell.

In certain embodiments of the invention, coding sequences are provided operably linked to a heterologous promoter, which exhibits a constitutive, root-preferred, or inducible pattern of gene expression. Expression constructs are also provided comprising these sequences, as are plants and plant cells transformed with the sequences.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of a plant disease resistance phenotype by genetic transformation with isoflavonoid and/or flavonoid biosynthesis genes. The FS or IFS biosynthesis gene, or regulatory transcription factor that enhances flavonoid biosynthesis, may be provided with other sequences, for instance, sequences that function as selectable or screenable markers. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), ocs (Herrera-Estrella et al, 1983), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989), those associated with the R gene complex (Chandler et al., 1989) or a constitutive promoter such as the T1275 promoter (e.g. U.S. Pat. No. 5,824,872) or a CsVMV promoter (e.g. Samac et al., 2004; U.S. Patent Applic. Publn. 2006/0041950). Tissue specific promoters such as root cell promoters (Conkling et al., 1990) and tissue specific enhancers (Fromm et al., 1986) are also contemplated to be particularly useful, as are inducible promoters such as ABA- and turgor-inducible promoters.

In some embodiments, the heterologous nucleic acid sequence is not expressed in the stem or foliage of the plant. In additional embodiments, the heterologous nucleic acid sequence is operably linked to a root-preferred promoter. In particular embodiments, the root-preferred promoter is an RB7, RPE15, RPE14, RPE19, RPE29, RPE60, RPE2, RPE39, RPE61, SHR, ELG3, EXP7, EXP18 or Atlg73160 promoter (e.g. WO 01/053502; Yamamoto et al., 1991; U.S. Patent Application Publication 2005/0257286). In other embodiments, the heterologous nucleic acid sequence may be expressed primarily in response to infection by a root-infecting fungal plant pathogen or mutualist. In some of those plants, heterologous nucleic acid sequence is operably linked to a fungal pathogen-inducible promoter. In particular embodiments, the fungal pathogen-inducible promoter is an hsr203J promoter, a PVS3 promoter, a NI16 promoter, a MtPT4 promoter, or a STS8 stilbene synthase promoter (e.g. Pontier et al., 1994; U.S. Pat. No. 6,072,103; U.S. Pat. No. 7,005,562; U.S. Patent Application Publication 2006/0053509). In some plants, a heterologous nucleic acid sequence is operably linked to a fungal mutualist-inducible promoter (e.g. MtPT4, Harrison et al., 2002; Gomez et al., 2009). In additional embodiments, the plant accumulates 7,4-dihydroxyflavone and/or medicarpin when contacted with *Phymatotrichopsis omnivora*.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is specifically envisioned that flavonoid or isoflavonoid biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an α-tubulin gene that also directs expression in roots.

B. Terminators

Transformation constructs prepared in accordance with the invention will typically include a 3' end DNA sequence that acts as a signal to terminate transcription and allow for the poly-adenylation of the mRNA produced by coding sequences operably linked to, for instance, a flavonoid or isoflavonoid biosynthesis gene. In one embodiment of the invention, the native terminator of a FS or IFS gene is used. Alternatively, a heterologous 3' end may enhance the expression of the flavonoid or isoflavonoid biosynthesis genes. Terminators which are deemed to be particularly useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable markers" also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening.

III. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bacto™ agar (Difco-BD, Franklin Lakes, N.J.), Hazleton agar (Hazleton, Lenexa, Kans., USA), Gelrite® (Sigma, St. Louis, Mo.), PHYTAGEL (Sigma-Aldrich, St. Louis, Mo.), and GELGRO (ICN-MP Biochemicals, Irvine, Calif., USA) are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, callus, immature embryos, hairy root cultures, and gametic cells such as microspores, pollen, sperm and egg cells. Callus may be initiated from tissue sources including, but not limited to, immature embryos, seedling apical meristems, root, leaf, microspores and the like. Those cells which are capable of proliferating as callus also are candidate recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population, for example by manual selection and culture of friable, embryogenic tissue. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., (1975) and MS media (Murashige and Skoog, 1962).

IV. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including Arabidopsis, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616), wheat (McCormac et al., 1998), barley (Tingay et al., 1997; McCormac et al., 1998), alfalfa (e.g. Thomas et al., 1990; McKersie et al., 1993; Chabaud et al., 1993) and maize (Ishida et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*- mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics® Particle Delivery System (Dupont), which can be used to propel particles coated with DNA or cells through a screen, such as a stainless steel or nylon screen (e.g. NYTEX screen; Sefar America, Depew, N.Y. USA), onto a filter surface covered with plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994), wheat (U.S. Pat. No. 5,563,055), and sorghum (Casa et al., 1993); as well as a number of dicots including tobacco (Tomes et al., 1990; Buising and Benbow, 1994), soybean (U.S. Pat. No. 5,322,783), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of plants from protoplasts have been described (Toriyama et al., 1986; Yamada et al., 1986; Abdullah et al., 1986; Omirulleh et al., 1993 and U.S. Pat. No. 5,508,184). Examples of the use of direct uptake transformation of protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128; (Thompson, 1995) and rice (Nagatani, 1997).

V. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,508,468).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cells or tissue types, a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soil-less plant growth mix, and hardened, e.g., in an environmentally controlled chamber, for example, at about 85% relative humidity, 600 ppm $CO_2$, and 25-250 microeinsteins $m^{-2}s^{-1}$ of light. Plants are preferably matured either in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plantcon™ containers (MP-ICN Biomedicals, Solon, Ohio, USA). Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$ M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note that intact sequences will not always be present, presumably due to rearrangement or deletion of sequences in the cell. The presence of DNA elements introduced through the methods of this invention may be determined, for example, by polymerase chain reaction (PCR). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR analysis. In addition, it is not typically possible using PCR™ techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

Whereas DNA analysis techniques may be conducted using DNA isolated from any part of a plant, RNA will only be expressed in particular cells or tissue types and hence it will be necessary to prepare RNA for analysis from these tissues. PCR techniques also may be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

E. Gene Expression

While Southern blotting and PCR may be used to detect the gene(s) in question, they do not provide information as to whether the corresponding protein is being expressed. Expression may be evaluated by determining expression via transcript-profiling techniques such as by use of a microarray, and by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VI. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected CT biosynthesis gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VII. Definitions

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene. A "constitutive promoter" allows for continual transcription of its associated gene. The term "constitutive" as used herein does not necessarily indicate that a gene is expressed at the same level in all cell types, but that the gene is expressed in a wide range of cell types, although some variation in abundance is often observed. An "inducible promoter" is a promoter that is capable activating transcription of one or more DNA sequences or genes in response to an inducer. The inducer can be, for instance, a chemical agent, a physiological stress or condition, or a pathogen.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule capable of replication in a host cell and/or to which another DNA segment can be operatively linked so as to bring about replication of the attached segment. A plasmid is an exemplary vector.

VIII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

Plant and Fungal Materials

*Phymatotrichopsis omnivora* (Stephen M. Marek, Oklahoma State University) was grown on wheat seeds for inoculation with plants or on PDA medium for fungal inhibition assays at 28° C. Seeds of *M. truncatula* ecotype Jemalong A17 were germinated and grown in Petri dishes containing Murashige and Skoog (MS) medium (Murashige and Skoog, 1962), under growth chamber conditions (29° C. day/16° C. night temperature; 16 h day/8 h night photoperiod; 70-80% relative humidity, and 150 µmol/m$^2$/s and 80 µmol/m$^2$/s light intensity). 4 to 5 week old *M. truncatula* plants were inoculated by placing a single *P. omnivora* infected wheat seed close to the plant root 5 mm below the medium surface. Plant root samples were collected at 1, 3, 5, 7, and 9 days post inoculation with 5 replicates for primary metabolite profiling, 4 replicates for secondary metabolite profiling and 3 replicates for real time PCR analysis for both control and infected plants. Plant samples were either lyophilized for 48-72 hr until dry and ground for further metabolite extraction or frozen immediately upon harvest and kept at −80° C. for RNA purification. PDA medium (Difco™ PDA 18 g/L, malt extract 1 g/L, yeast extract 1 g/L and peptone 1 g/L) nutrients were purchased from Phytotechnology Lab (Shawnee Mission, Kans.) except malt extract which was purchased from Fluka (Milwaukee, Wis.). Vitamins for MS medium (0.15% Difco™ agar and 2% sucrose) were purchased from Phytotechnology Lab (Shawnee Mission, Kans.).

All solvents used were HPLC-MS or GC-MS grade. Flavonoid and isoflavonoid aglycones and glycoside conjugate standards were purchased from Indofine (Hillsborough, N.J.) or ChromaDex (Santa Ana, Calif.) except as described below. (−)-Medicarpin was purified from alfalfa roots as described previously (Kessmann et al., 1990).

EXAMPLE 2

GC/MS Analysis of Plant Primary Metabolites and UPLC/UV/ESI-MS Analysis of Plant Secondary Metabolites Dried plant samples were homogenized with a bead beater, and 6.0-6.05 mg of dried tissue was weighed into a 4.0 ml glass vial. A portion of 1.5 mL chloroform containing 10 mg/mL docosanol (internal standard) was added to dried mycelia. The sample was thoroughly vortexed and incubated for 45 min at 50° C. After equilibrating to room temperature, 1.5 ml of HPLC-grade water containing 25 mg/mL ribitol was added to the chloroform. The sample was further vortexed, and incubated for an additional 45 min. The biphasic solvent system was then centrifuged at 2900 g for 30 min at 4° C. to separate the organic and aqueous layer. One ml of each layer was collected and transferred to individual 2.0 mL autosampler vials. The chloroform layer (non-polar) was dried under nitrogen and the aqueous layer dried in a speed vacuum centrifuged at ambient temperature for 2-3 h.

The non-polar layer was resuspended in 0.8 mL chloroform and hydrolyzed by adding 0.5 mL 1.25 M HCl in MeOH and incubating for 4 h at 50° C. Following hydrolysis, HCl and solvent were evaporated under nitrogen. The sample was resuspended in 30 µL pyridine and derivatized through the addition of 20 µL of a commercial derivatization solution containing MSTFA+1% TMCS (Pierce Biotechnology, Rockford, Ill., USA). The sample was incubated for 1 h at 50° C. to allow thorough derivatization. The sample was equilibrated to room temperature, transferred to a 200 µL glass insert, and analyzed using an Agilent 6890 GC coupled to a 5973 MSD scanning from m/z 50-650. Samples were injected at a 1:1 split ratio, and the inlet and transfer line were held at 280° C. Separations were achieved using a 60 m DB-5 MS column (J&W Scientific, 0.25 mm internal diameter, 0.25 µm film thickness), a temperature program of 80° C. for 2 min then ramped at 5° C./min to 315° C. and held for 12 min, and a constant flow of He at 1.0 ml/min.

Dried polar extracts were methoximated in pyridine with 40 µL of 15.0 mg/mL methoxyamine-HCl, vortexed thoroughly and sonicated for 15 min at room temperature, followed by incubation at 50° C. until the residue was resuspended (approximately 2 h). Metabolites were then derivatized with 40 µL of MSTFA+1% TMCS for 1 h at 50° C. The sample was subsequently transferred to a 300 µL glass insert and analyzed by GC-MS using the same parameters as described for the non-polar extracts, with the exception that the injection split ratio was set to 15:1 for polar samples.

For analysis of secondary metabolites, dried plant samples were homogenized with a bead beater, and 5.0-5.05 mg of dried tissue was weighed into a 2.0 ml glass vial and extracted with 0.5 mL 80% CH$_3$OH solution containing 0.5 µg/mL of umbelliferone as internal standard. A 0.4 mL aliquot of the extract was concentrated to 50 µL and analyzed with a UPLC (Waters) equipped with a photodiode array detector and coupled to a LECO Unique TOF-MS. A portion of 5 µL was injected onto a reverse-phase column (ACQUITY UPLC™ BEH C18 1.7 µm, 2.1 mm×150 mm), which was maintained at 60° C. and components were eluted using a linear gradient from 95% to 30% A (eluent A, 0.1% aq. HOAc) over 30 min and a flow rate of 0.56 mL/min. The complementary eluent B was acetonitrile. TOF-MS spectra were acquired using a spectral acquisition rate 3.13 per second; detector voltage 2600 (v); threshold 2037; ESI–4500 v; desolvation temperature 300° C.; nebulizer pressure 350 kPa; and interface 100° C. Mass accuracy was within 20 ppm.

Relative metabolite abundances were calculated using publically available Metabolomics Ion based Data Extraction Algorithm (MET-IDEA) software (www.bioinfo.noble.org/download) (Broeckling et al., 2006) to extract relative peak areas of individual ions characteristic of each component. Metabolites were identified through spectral and retention time matching with authentic compounds prepared in an identical manner, and further confirmed through spectral matching against the National Institutes of Standards and Technology (NIST) library. Peak areas were normalized by dividing each peak area value by the mean peak area of the internal standard. Metabolite variance was calculated based on the ratio of the average peak area of infected and control plant samples. Hierarchical Clustering Analysis (HCA) was performed using Spotfire (http://spotfire.tibco.com/). Principal component analysis (PCA) was performed on normalized datasets using Pirouette software (InfoMetrix, Woodinville, Wash.). Results are shown in Example 4.

EXAMPLE 3

PCR Methods

All PCR primers listed in Table 1 contain 20-26 nucleotides with GC content of 40-60% and were designed to amply 60-150 bp fragments, using Primer3 Express software (http://www.frodo.wi.mit.edu/cgi-bin/primer3/primer3_www.cgi). The specificity of the primer pair sequences used to analyze expression of genes in the flavonoid and isoflavonoid biosynthetic pathways was checked against the M. truncatula transcript database using nucleotide-nucleotide BLAST (e.g. Altschuhl et al., 1997; www.ncbi.nlm.nih.gov/BLAST/).

the transcript levels were determined by relative quantification (Pfaffl, 2001) using the ubiquitin gene (TC102473 from the Medicago truncatula Gene Index; e.g. Kakar et al., 2008) as reference.

EXAMPLE 4

Metabolomics Assessment of M. Truncatula and P. Omnivora Interaction

Phymatotrichopsis omnivora was cultivated on wheat seeds and individual M. truncatula seedlings were inoculated with a single infected or uninfected (control) wheat seed. Plant roots inoculated with the fungus darken at 3 days post inoculation (DPI), a positive indicator of infection and necrosis, while control roots inoculated with uninfected wheat seeds remained normal. The infected root area progressed over time until the entire main root became black and necrotic. Infected plant aerial tissues started wilting at 9 days and eventually died at approximately 11 DPI (FIG. 2). Individual plant root samples were collected between 0 to 9 DPI at 6 different time points with 12 replicates for each control and infected plants. Of the 12 samples, 5 replicates were used for primary metabolite profiling, 4 for secondary metabolite profiling, and 3 for the measurement of gene expression levels with quantitative RT-PCR.

Primary metabolites were fractionated into polar and nonpolar fractions using a bi-phasic $H_2O$ and $CHCl_3$ extraction, which were then analyzed independently using GC-MS following derivatization. Secondary metabolites were extracted using 80% $CH_3OH$ in water and analyzed with a UPLC-TOFMS. GC-MS chromatograms were deconvoluted with Automated Mass Spectral Deconvolution and Identification System (AMDIS) software freely available from NIST (http://chemdata.-nist.gov/mass-spc/amdis/) (Stein, 1999), while UPLC-qTOFMS data were deconvoluted using propri-

TABLE 1

Primers for RT-PCR (SEQ ID NOs: 12-23).

| genes | Forward | SEQ ID NO: | Reverse | SEQ ID NO: |
|---|---|---|---|---|
| CHS | CCACGACACCATCCTAAATTGTATC | 12 | TGGTGTGACTAATGCCTTTTTGAC | 13 |
| CHR | GCAACGCAAACGGAATAGTGT | 14 | TGGTCCTCTGCTTGCACCTT | 15 |
| CHI | CACGCTGTTTCCCCTGATCT | 16 | TCAACAACGCCGGTAATCTTG | 17 |
| IFS | GTGAAGGAGGTATTCCGTTTGC | 18 | TCTCACACTCTTCGGTGCATTT | 19 |
| FS | CAGCAGGAACAGACACAACATCA | 20 | TGAAGGGTTGTTCATTAGCTCAAC | 21 |
| VR | TTGGTGGTCGTTTTGTTTGC | 22 | CCCTAATACCAAAACAAGAGCTTTC | 23 |

Total RNA was isolated from plant roots using RNeasy™ Plant Mini Kit (Qiagen Science, Valencia, Calif.). Quantitative RT-PCR was performed according to published methods (Czechowski et al., 2005) by The Noble Foundation, Genomic and Microarray facility (www.noble.org/CoreFacilities/Genomics/index.html) using an ABI 7900HT sequence detection system (Applied Biosystems, Foster City, Calif.). Data were analyzed using the SDS 2.2.1 software (Applied Biosystems). PCR efficiency (E) was estimated using the LinRegPCR software (Ramakers et al., 2003) and etary Leco software (LECO, St. Joseph, Mich.). Ion and retention time pairs obtained through deconvolution were then transferred to the custom software MET-IDEA (http://bioinfo.noble.org/download; (Broeckling et al., 2006)) for high through-put quantitative data extraction and statistical analyses.

Figure 6:
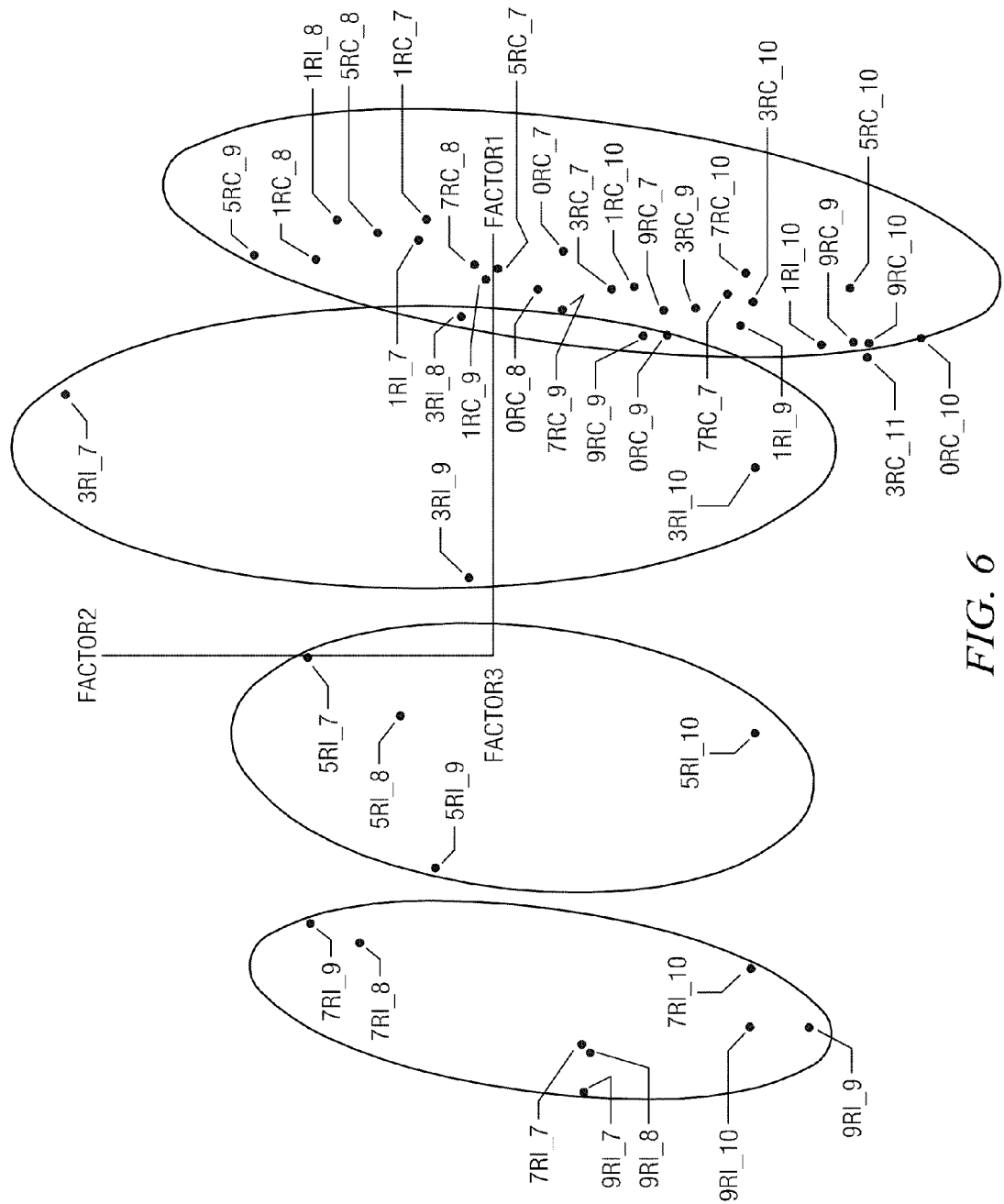
FIG. 6. Principal component analysis (PCA) plot of the secondary metabolite profiles (illustrated as various colored dots with an abbreviated nomenclature composed of days post inoculation, root (R), and control (C) vs. inoculated (I), i.e. 9RI represents profile of roots 9 day post inoculation) with x-y-z axes representing the first three principal components.

The majority of observed primary metabolites showed a biological variance below 50%, and the secondary metabolites less than 30%, which is comparable with previous reports (Sumner et al., 2003; Schliemann et al., 2008). Principal component analysis (PCA) of UPLC-TOFMS data was performed and plotted in FIG. 6. PCA summarizes the similarity and differences in a set of multivariate data in terms of a set of underlying orthogonal variables (i.e. principal components). The original variables (metabolite concentrations) can be expressed as a particular linear combination of the principal components. PCA is a linear additive model, in the sense that each principal component (PC) accounts for a portion of the total variance of the data set. Often, a small set of principal components (2 or 3) account for over 90% of the total variance, and in such circumstances, one can resynthesize the data from those few PCs and thus reduce the dimension of the data set. Plotting the data in the space defined by the two or three largest PCs provides a rapid means of visualizing similarities or differences in the data set, perhaps allowing for improved discrimination of samples. Thus, FIG. 6 is a plot of the cumulative metabolite profiles (illustrated as various colored dots with an abbreviated nomenclature of days post inoculation, root (R), and control (C) vs. inoculated (I), i.e. 9RI represents profile of roots 9 day post inoculation) with axes representing the first three principal components. FIG. 6 illustrates high similarity within all the controls which co-clustered relative to the infected tissues. Metabolic differences between control and infected plants were observed starting at 3 days post inoculation and these differences increased until 9 DPI. The temporal changes were also revealed in the PCA analyses as a clear trajectory of the infected samples away from the controls.

Hierarchical cluster analysis (HCA) is a method of grouping samples in a data set by their similarity and involves a progressive pair-wise grouping of samples by distance. Several distance measures can be used in HCA, such as Euclidean distance, Manhattan distance, or correlation. The result of hierarchical clustering is usually visualized as a dendrogram or a tree. Branch lengths can be made proportional to the distances between groups. This can provide an easy visualization of the similarities of samples within data sets. HCA was performed on the resultant metabolite profiles and the results are plotted in FIG. 7 as relative quantitative ratios of the root infected vs. control (x-axis) for each metabolite (y-axis). The HCA analyses revealed substantial metabolic differences in plant roots in response to fungal infection (FIG. 7) and accumulation level of most primary and secondary metabolites changed more than 2 fold at 7 DPI.

EXAMPLE 5

Accumulation of Primary Metabolites in Plant Roots Upon Fungal Infection

Primary metabolites were identified based on spectral and retention time matching with authentic compounds contained within a custom in-house EI-MS library containing over 600 primary metabolites. These identifications were further confirmed through spectral matching against the National Institutes of Standards and Technology (NIST) library. The polar profiles contained mainly primary polar metabolites including amino acids, organic acids, nucleotides, sugars and sugar alcohols (Table 2). The temporal changes are represented as relative ratios (control relative to inoculated) for each metabolite from 0 to 9 days post inoculation (DPI) with *P. omnivora*. Molecules were profiled with GC/MS and identified according to retention time (R.T.) and MS/EI spectra based on an in house library. Each molecule was quantified with in-house software MET-IDEA and was based on the intensity of its typical ion by comparison to the internal standard, ribitol.

TABLE 2

The kinetics of primary metabolites accumulated in *M. truncatula* root inoculated with and without *P. omnivora* at different time points. Significant changes are bolded for increases and italicized for decreases.

| compound | R.T. | ion | 0R_ratio | 1R_ratio | 3R_ratio | 5R_ratio | 7R_ratio | 9R_ratio |
|---|---|---|---|---|---|---|---|---|
| AMINO ACIDS | | | | | | | | |
| L-Valine | 12.2409 | 174 | 1 | 1.3255487 | 1.2109139 | 1.5506149 | 4.4186493 | 2.0148729 |
| N-Butylamine | 12.751 | 202 | 1 | 1.0638754 | 0.9346743 | 1.040231 | 1.214741 | 1.3217414 |
| L-Leucine | 14.1295 | 86 | 1 | 1.4361001 | 1.1037681 | 1.6915202 | 1.4792925 | 6.0534829 |
| L-Isoleucine | 14.766 | 86 | 1 | 1.6103661 | 1.2225259 | 1.6646706 | 1.1055893 | 5.8010811 |
| L-Serine | 16.8987 | 219 | 1 | 0.7094382 | 0.8935716 | 1.3339242 | 1.4634057 | 1.1655492 |
| L-Threonine | 17.9174 | 219 | 1 | 1.1637467 | 1.7832145 | 1.2921335 | 2.9618267 | 4.147867 |
| L-Proline* | 18.088 | 142 | 1 | 0.5552014 | 1.1972784 | 1.6185487 | 7.6555729 | 7.4708042 |
| L-Glycine | 18.287 | 174 | 1 | 0.4068567 | 1.1477139 | 3.4415535 | 8.4807734 | 9.5883813 |
| L-Alanine | 19.7499 | 188 | 1 | 1.1539713 | 2.8786468 | 9.1827736 | 10.395502 | 6.4295202 |
| L-Threonine | 20.2964 | 218 | 1 | 1.0794555 | 1.0742867 | 1.0216892 | 1.8108227 | 2.5379635 |
| L-Aspartic Acid (2TMS) | 21.4095 | 160 | 1 | 1.1750432 | 1.1638372 | 3.0104075 | 2.6841621 | 6.4012419 |
| beta-Alanine | 21.514 | 248 | 1 | 0.8884024 | 1.0757231 | 3.3684718 | 5.3391386 | 2.1284132 |
| *L-Homoserine* | *21.9865* | *218* | *1* | *0.8395712* | *0.5889182* | *0.6723506* | *0.4245684* | *0.7367* |
| L-Aspartic Acid (3TMS) | 23.756 | 232 | 1 | 0.9502371 | 1.3392304 | 1.5084655 | 2.4447332 | 2.4424295 |
| L-Methionine | 23.8371 | 176 | 1 | 0.9237785 | 0.8290081 | 0.9701226 | 1.0616895 | 0.9647154 |
| Pyroglutamic Acid | 23.9246 | 230 | 1 | 1.5027204 | 1.3466072 | 1.9037156 | 1.7997938 | 1.3269214 |
| 4-Aminobutyric acid | 24.104 | 174 | 1 | 1.4990022 | 1.9584711 | 5.4904182 | 9.7423549 | 1.8418967 |
| *L-Asparagine* | *25.7336* | *159* | *1* | *1.0333827* | *0.785371* | *1.20177* | *0.3037305* | *0.0611955* |
| L-Glutamic Acid | 26.1597 | 246 | 1 | 1.5108048 | 2.0038568 | 2.957717 | 4.3776176 | 2.4309623 |
| L-Phenylalanine | 26.4614 | 218 | 1 | 1.1058045 | 1.0858692 | 1.1774537 | 1.4068026 | 1.6702445 |
| *L-Asparagine (3TMS)* | *27.3425* | *231* | *1* | *1.1507129* | *0.7837785* | *0.7645851* | *0.3429736* | *0.0200864* |
| *L-Putrescine* | *28.9452* | *214* | *1* | *1.4426644* | *1.4869041* | *0.7429326* | *0.4909917* | *0.1198679* |
| Ornithine | 30.5686 | 174 | 1 | 0.8358521 | 0.7241199 | 1.0667589 | 2.4313389 | 4.0479275 |
| *L-Arginine* | *30.7234* | *256* | *1* | *0.8964904* | *0.5705464* | *0.6226154* | *0.489826* | *0.2510226* |
| *L-Asparagine (4TMS)* | *31.6783* | *188* | *1* | *1.1176093* | *0.9994339* | *0.8489267* | *0.1376194* | *0.015352* |
| L-Lysine | 32.7316 | 174 | 1 | 0.8483306 | 0.8929885 | 0.929874 | 2.0560857 | 3.3138394 |
| L-Tyrosine | 33.0985 | 218 | 1 | 1.1650787 | 1.5671033 | 1.8605546 | 3.189044 | 6.4269953 |
| L-Glutamine | 34.2555 | 227 | 1 | 1.2528221 | 0.977785 | 1.2600155 | 0.5922376 | 0.4757403 |
| L-Tryptophan | 38.322 | 202 | 1 | 0.9562196 | 0.6551303 | 0.7604809 | 0.6177042 | 0.5666218 |

TABLE 2-continued

The kinetics of primary metabolites accumulated in *M. truncatula* root inoculated with and without *P. omnivora* at different time points. Significant changes are bolded for increases and italicized for decreases.

| compound | R.T. | ion | 0R_ratio | 1R_ratio | 3R_ratio | 5R_ratio | 7R_ratio | 9R_ratio |
|---|---|---|---|---|---|---|---|---|
| SUGARS | | | | | | | | |
| Xylose | 26.8581 | 307 | 1 | 1.0951095 | 0.6144737 | 0.5521887 | 0.7388965 | 1.8384652 |
| D-(−)-Ribose | 27.0225 | 307 | 1 | 1.152779 | 1.0341658 | 1.1635472 | 1.3545277 | 0.5624839 |
| *Arabinose* | *27.3493* | *188* | *1* | *1.133327* | *0.7821683* | *0.7904172* | *0.3224262* | *0.0193306* |
| 1,6-Anhydroglucose | 28.0748 | 204 | 1 | 1.2400307 | 1.2536181 | 1.2889249 | 0.825921 | 0.8497926 |
| Fructose methoxyamine | 31.5752 | 217 | 1 | 0.9034736 | 1.8993501 | 1.615204 | 2.9986566 | 5.6659168 |
| D-(+)-Mannose | 31.8669 | 319 | 1 | 1.3850002 | 1.5382952 | 1.8699991 | 1.5286628 | 1.067829 |
| Galactose | 32.5149 | 205 | 1 | 0.9572974 | 1.583403 | 1.3540312 | 1.9702611 | 1.4537758 |
| 1-Methyl-beta-D-galacto-pyranoside | 33.1292 | 204 | 1 | 1.8248334 | 0.8073236 | 0.9876055 | 1.1851631 | 1.7023898 |
| *Galactose/D-(+)-Mannose* | *36.2287* | *319* | *1* | *1.2731622* | *0.7245264* | *0.5706329* | *0.3343455* | *0.0920135* |
| Galactose | 36.5186 | 217 | 1 | 0.9648673 | 1.0528248 | 0.8165456 | 1.1634544 | 0.1903496 |
| 2-O-Glycerol-beta-D-galacto-pyranoside | 36.9222 | 204 | 1 | 1.4263219 | 0.9163863 | 0.7033425 | 0.6052392 | 0.16892 |
| Gulose | 37.421 | 217 | 1 | 1.4553524 | 0.9303705 | 0.7265172 | 0.5639855 | 0.1403717 |
| alpha-D-Gal-(1,3)-myo-Inositol | 39.3657 | 217 | 1 | 2.2585865 | 1.2980068 | 0.6585776 | 0.8050084 | 0.1559934 |
| *Cellobiose* | *41.5836* | *204* | *1* | *1.3987335* | *0.953609* | *0.5876256* | *0.268381* | *0.0570574* |
| *Melibiose* | *42.7063* | *204* | *1* | *1.0444333* | *0.9226357* | *0.8427395* | *0.4853961* | *0.3526414* |
| Lactose | 43.524 | 204 | 1 | 1.2339373 | 0.9694111 | 0.8886487 | 0.9069321 | 0.2039408 |
| *Sucrose* | *44.9271* | *361* | *1* | *1.1921487* | *1.2300115* | *1.1226687* | *0.5020931* | *0.0467311* |
| Maltose | 46.2356 | 361 | 1 | 1.0255772 | 1.2235262 | 1.4473789 | 1.8405866 | 2.5805098 |
| Trehalose | 46.5213 | 191 | 1 | 1.3845883 | 1.4660044 | 3.3131948 | 15.70795 | 16.21689 |
| SUGAR ALCOHOLS | | | | | | | | |
| Glycerol | 17.2303 | 205 | 1 | 0.9273327 | 1.0975452 | 0.8870058 | 1.0410111 | 1.063029 |
| Erythritol | 23.1496 | 217 | 1 | 1.203927 | 0.9554597 | 0.9089803 | 2.4493916 | 0.840125 |
| *Xylitol* | *27.8368* | *319.1* | *1* | *1.1576709* | *0.8481572* | *0.7092577* | *0.338301* | *0.0851916* |
| D-(+)-Arabitol | 28.318 | 217 | 1 | 3.2444392 | 2.8548288 | 4.5214846 | 8.2487325 | 14.271757 |
| *Pinitol* | *30.7601* | *318* | *1* | *1.0265253* | *0.7526255* | *0.5742032* | *0.4116958* | *0.1606953* |
| D-Mannitol | 32.7649 | 319 | 1 | 3.4762387 | 9.0586292 | 32.616079 | 101.46466 | 156.13277 |
| *Ononitol* | *55.5252* | *318* | *1* | *1.2686333* | *1.081352* | *0.3745872* | *0.2005438* | *0.0582964* |
| 4-O-Methyl-myo-inositol | 34.2057 | 305 | 1 | 1.2089231 | 1.3018882 | 0.8295601 | 0.5537706 | 0.3725527 |
| scyllo-Inositol (6TMS) | 34.698 | 318 | 1 | 1.1780099 | 1.1016646 | 0.8154154 | 1.4118923 | 1.4615367 |
| *Myo-Inositol* | *35.9475* | *305* | *1* | *1.4185858* | *1.0047995* | *0.7343996* | *0.3120965* | *0.1605843* |
| 2-O-Glycerol-beta-D-galactopyranoside | 37.5381 | 204 | 1 | 1.1841124 | 0.5291556 | 1.2172115 | 0.8050753 | 0.6842514 |
| ORGANIC ACIDS | | | | | | | | |
| Propanoic Acid = pyruvic acid | 11.0322 | 174 | 1 | 0.8069137 | 0.8954904 | 0.8841826 | 1.2654895 | 0.7115527 |
| Lactic Acid | 11.3011 | 191 | 1 | 0.0699621 | 1.3419061 | 1.2274573 | 1.9945851 | 1.9505671 |
| Glycolic Acid = hydroxyacetic acid | 11.7581 | 205 | 1 | 1.0533911 | 1.2721992 | 1.1276783 | 1.4224024 | 1.7972252 |
| Malonic acid | 15.3626 | 233 | 1 | 0.9656534 | 0.8410611 | 1.005267 | 0.8944213 | 0.2812321 |
| Phosphoric Acid | 17.216 | 299 | 1 | 0.9067039 | 1.1440633 | 0.8829252 | 0.8935989 | 0.5524659 |
| Succinic Acid | 18.462 | 247 | 1 | 1.0762534 | 1.4129795 | 2.3671754 | 5.2385339 | 6.2946214 |
| *Glyceric Acid* | *18.7882* | *292* | *1* | *0.9700418* | *1.0763673* | *1.0211946* | *0.6612716* | *0.3675543* |
| Malic Acid | 22.9414 | 233 | 1 | 0.9302367 | 1.1097251 | 1.4456988 | 1.583201 | 1.1188785 |
| *Threonic acid* | *24.2255* | *292* | *1* | *1.1742269* | *0.8460753* | *0.4106821* | *0.2128117* | *0.0464422* |
| *Fumaric acid* | *24.334* | *245* | *1* | *1.0994936* | *0.9172381* | *0.9267947* | *0.4351726* | *0.1589699* |
| *Ribonic acid* | *29.0774* | *292* | *1* | *1.4049501* | *0.7095016* | *0.3870279* | *0.1985808* | *0.1741475* |
| *2-Keto-L-gluconic acid* | *29.3327* | *292* | *1* | *1.0828739* | *0.7778973* | *0.4059567* | *0.2097428* | *0.0345733* |
| *Dihydroorotic acid* | *29.5997* | *257* | *1* | *1.1530847* | *0.9227798* | *0.9396417* | *0.5355014* | *0.1261217* |
| Galactaric Acid | 30.2692 | 333 | 1 | 1.1746021 | 0.9781847 | 0.7209889 | 1.4303588 | 1.1517912 |
| *Gluconic acid* | *33.4876* | *319* | *1* | *0.9764715* | *0.5323763* | *0.4770558* | *0.3262426* | *0.3356581* |
| *Galactonic acid* | *34.0863* | *292* | *1* | *1.1956203* | *1.0183118* | *0.5332264* | *0.2849984* | *0.2744227* |
| *Glucaric Acid* | *34.4367* | *292* | *1* | *1.5348375* | *0.6105771* | *0.353705* | *0.2489257* | *0.0616302* |
| *Saccharic Acid = Glucaric acid* | *35.0017* | *333* | *1* | *1.0625589* | *0.6160944* | *0.4398249* | *0.3209317* | *0.1964197* |
| *Deoxy-arabino-hexaric acid* | *36.1763* | *245* | *1* | *1.3181532* | *0.5997355* | *0.5386544* | *0.3995724* | *0.1472892* |

Of the 21 protein amino acids, only histidine and cysteine were not detected with these methods. Most of the protein amino acids including threonine, aspartic acid, valine, glutamic acid, glycine, alanine, lysine and proline accumulated at higher levels in infected plant roots starting at 5 DPI until 7 DPI with modest progressive changes observed at 9 DPI. Glycine and alanine increased the most (more than 8-fold) and proline, a recognized stress osmoprotectant, increased 7-fold at 7 DPI. Interestingly, the accumulation patterns of the 3 aromatic amino acids were different and tyrosine increased more than 3-fold and tryptophan decreased 2-fold at 7 DPI, but phenylalanine, the entry point for phenylpropanoid pathway, showed no obvious change. Leucine and isoleucine levels showed no obvious changes during early stages of infection; but suddenly increased at 9 DPI. Non-protein amino acids including homoserine, pyroglutamic acid, α-alanine and 4-aminobutyric acid were detected and levels of the last two increased. Levels of serine and methionine did not display significant changes, while arginine and asparagine levels decreased throughout the time course.

Sucrose accumulated 3-fold less in infected plant roots at 7 DPI, and more than 20-fold less at 9 DPI. The decreased accumulation of sucrose also correlated with decreased levels of D-glucose, galactose, arabinose, and ribose. However, not all monosaccharides were reduced in infected plant roots and D-fructose increased more than 5-fold at 9 days. The levels of several disaccharides including melibiose, cellobiose and lactose also decreased. However, two disaccharides, maltose and trehalose, increased upon fungal infection. Trehalose, an osmoprotectant, accumulated 3-fold higher at 5 days and increased by more than 15-fold at 7 and 9 DPI.

Increased fructose levels could contribute to the synthesis of mannitol, which accumulated to a much higher level at 1 DPI, and the ratio of mannitol levels at 9 DPI in infected to control plant increased more than 100-fold.

Non-polar molecules extracted with $CHCl_3$ were first hydrolyzed with $HCl/CH_3OH$ to release fatty acids and/or various head groups from lipids, which were then derivatized with MSTFA prior to GC/MS analysis. The most abundant molecules detected in this fraction were fatty acids, fatty acid alcohols, and long chain alkanes. Changes in GC-MS non-polar metabolite levels between control and infected plant samples were not as dramatic as the polar primary metabolites extracted with $H_2O$. However, three fatty acids, palmitic acid, heptadecanoic acid and 15-octadecenoic acid levels increased 2 to 4-fold higher in infected roots before 9 DPI. Fatty acids observed by UPLC-QTOFMS were tentatively identified according accurate mass, and sterculic acid and colneleic acid increased the most. These divinyl ether fatty acids have also been reported to increase in potato during fungal late-blight pathogen (*Phytophthora infestans*) infection and are inhibitory to *P. infestans* (Weber et al., 1999). All other fatty acids showed minimal differences upon fungal infection.

EXAMPLE 6

Accumulation of Secondary Metabolites in Plant Roots Upon Fungal Infection

The accumulation of antimicrobial phytoalexins and other secondary metabolites are commonly associated with plant-pathogen interactions (Dixon, 2001). *M. truncatula* root secondary metabolites were extracted with 80% aqueous $CH_3OH$ and analyzed with a Waters UPLC with online PDA detection coupled to a LECO ESI-TOFMS. Identification of secondary metabolites was based upon comparison of MS, RT, and UV characteristics relative to authentic standards. UPLC-QTOFMS data were deconvoluted with proprietary LECO software and quantitative data were extracted with MET-IDEA. The majority of compounds showed a biological variance below 30%.

Figure 4A:
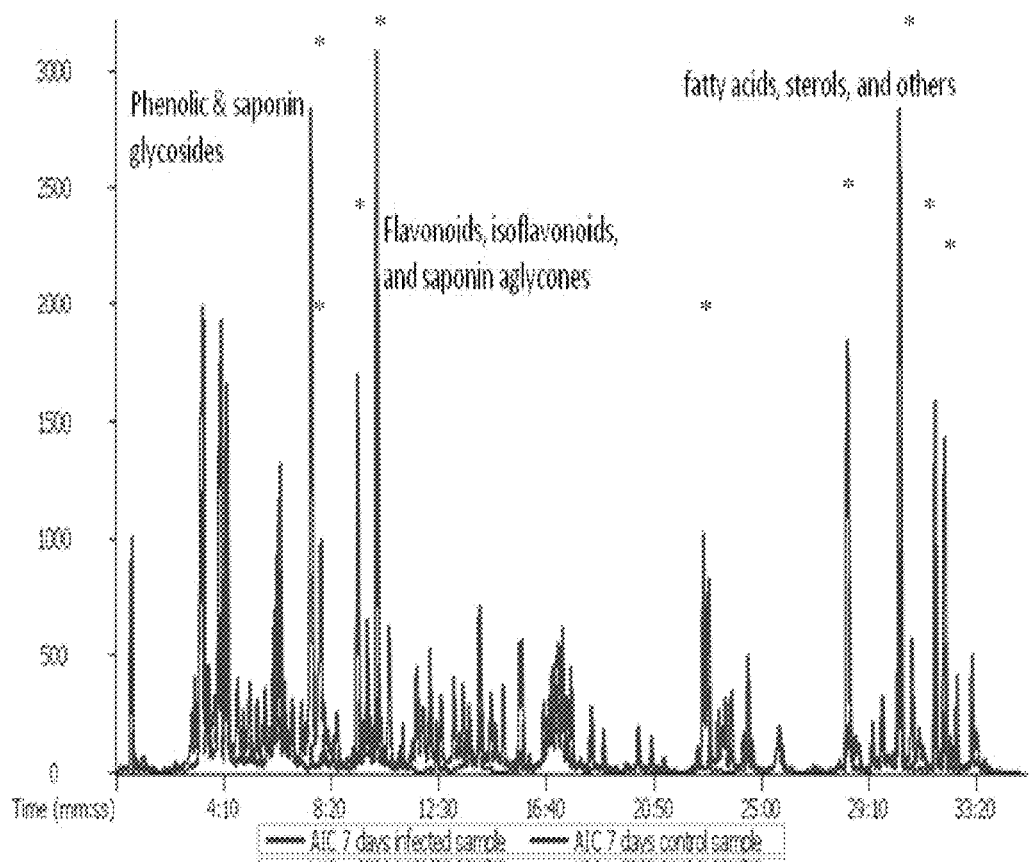
FIG. 4. (A) Comparative UPLC-TOFMS metabolite profiles of control and infected plant roots illustrating the dramatic changes in secondary metabolism induced in *M. truncatula* seven days post inoculation with *P. omnivora*. An "*" indicates a prominent peak for the infected sample. (B) Relative quantitative changes of specific chalcones, isoflavones, and flavones.
Figure 4B:
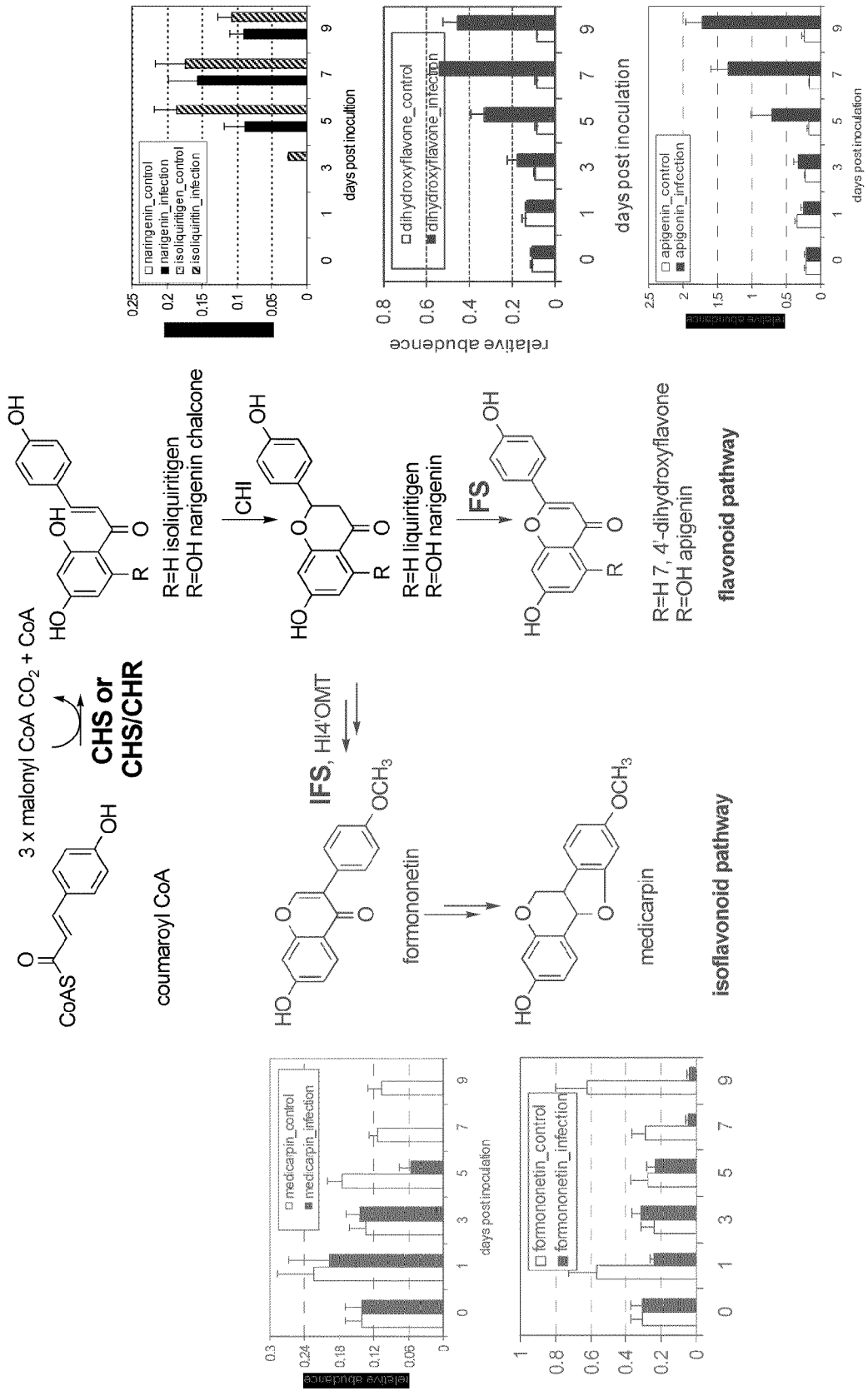
Figure 7:
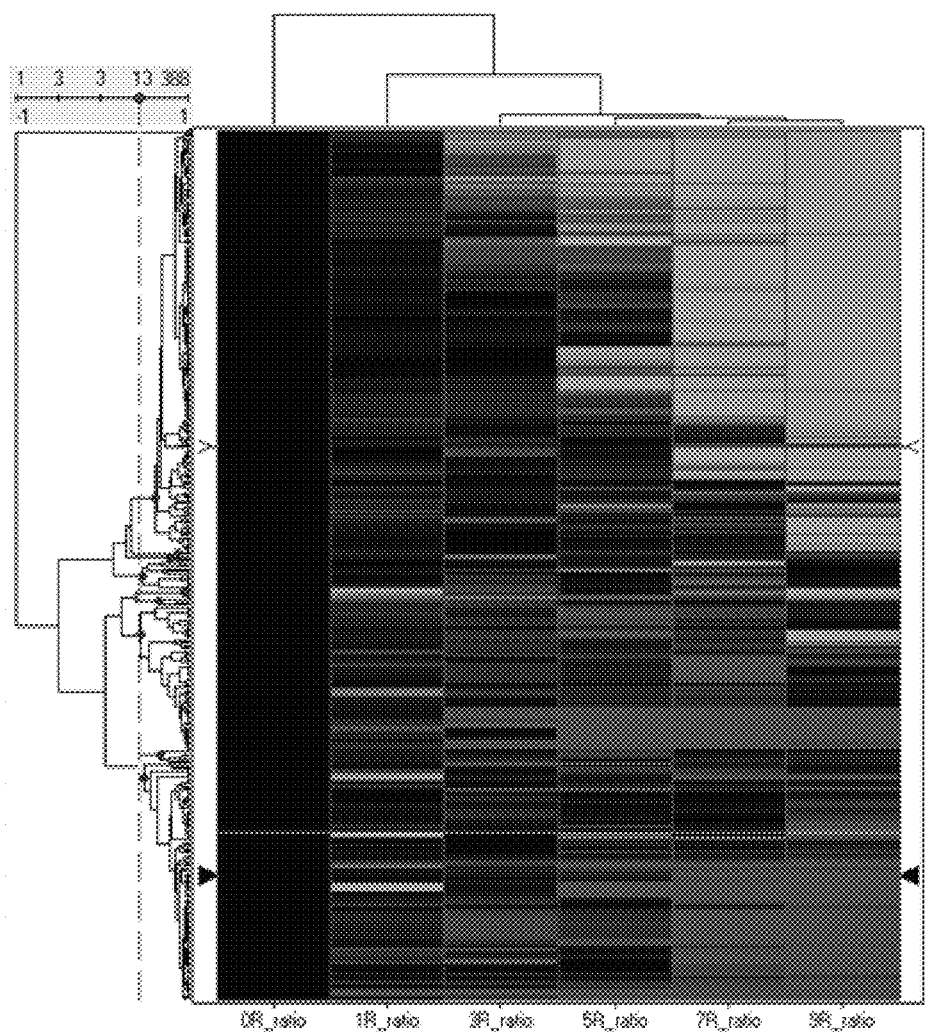
FIG. 7. Hierarchical cluster analysis (HCA) analysis of primary and secondary metabolite profiling revealing substantial metabolic differences in plant roots in response to *P. omnivora* infection. The results are plotted as relative quantitative ratios of the root infected vs. control (x-axis) for each metabolite (y-axis).
Figure 7:
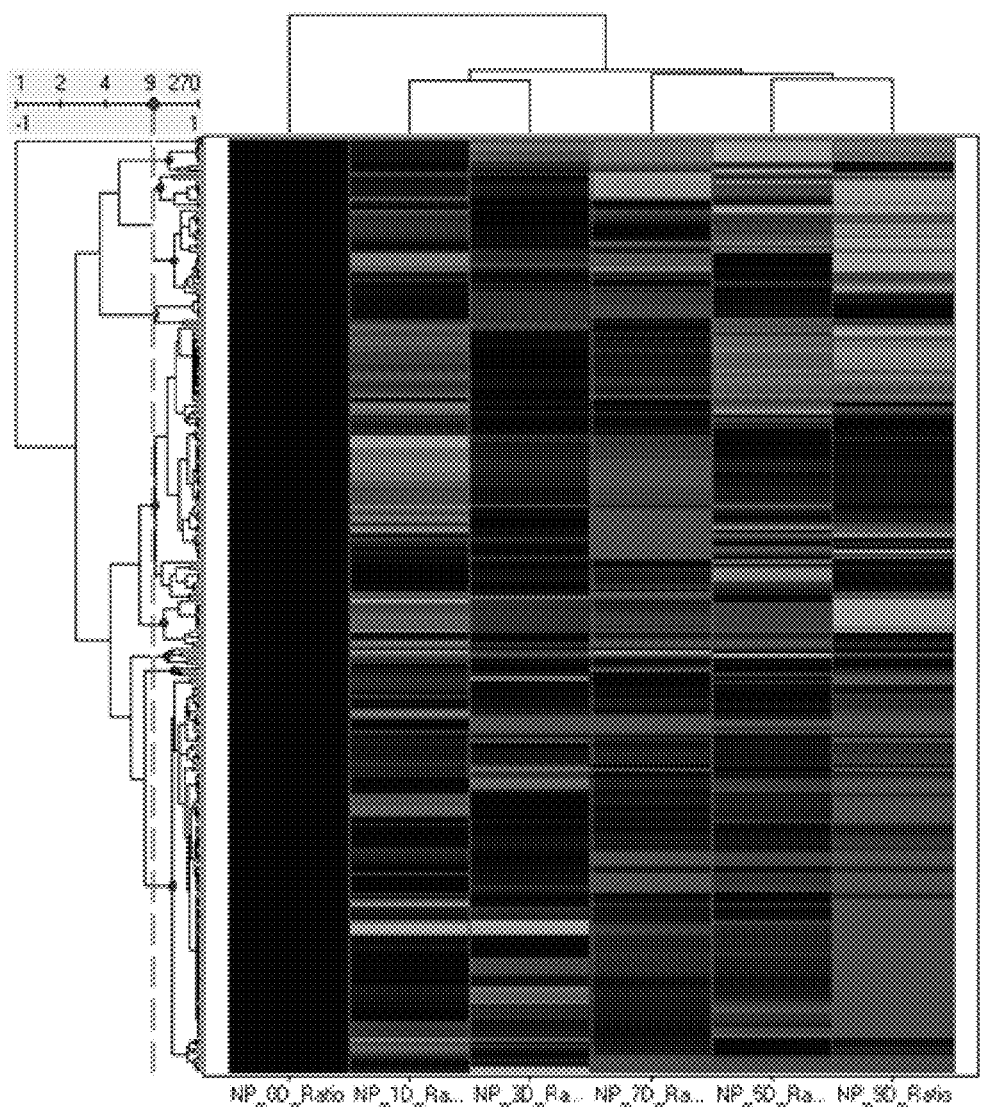
Figure 7:
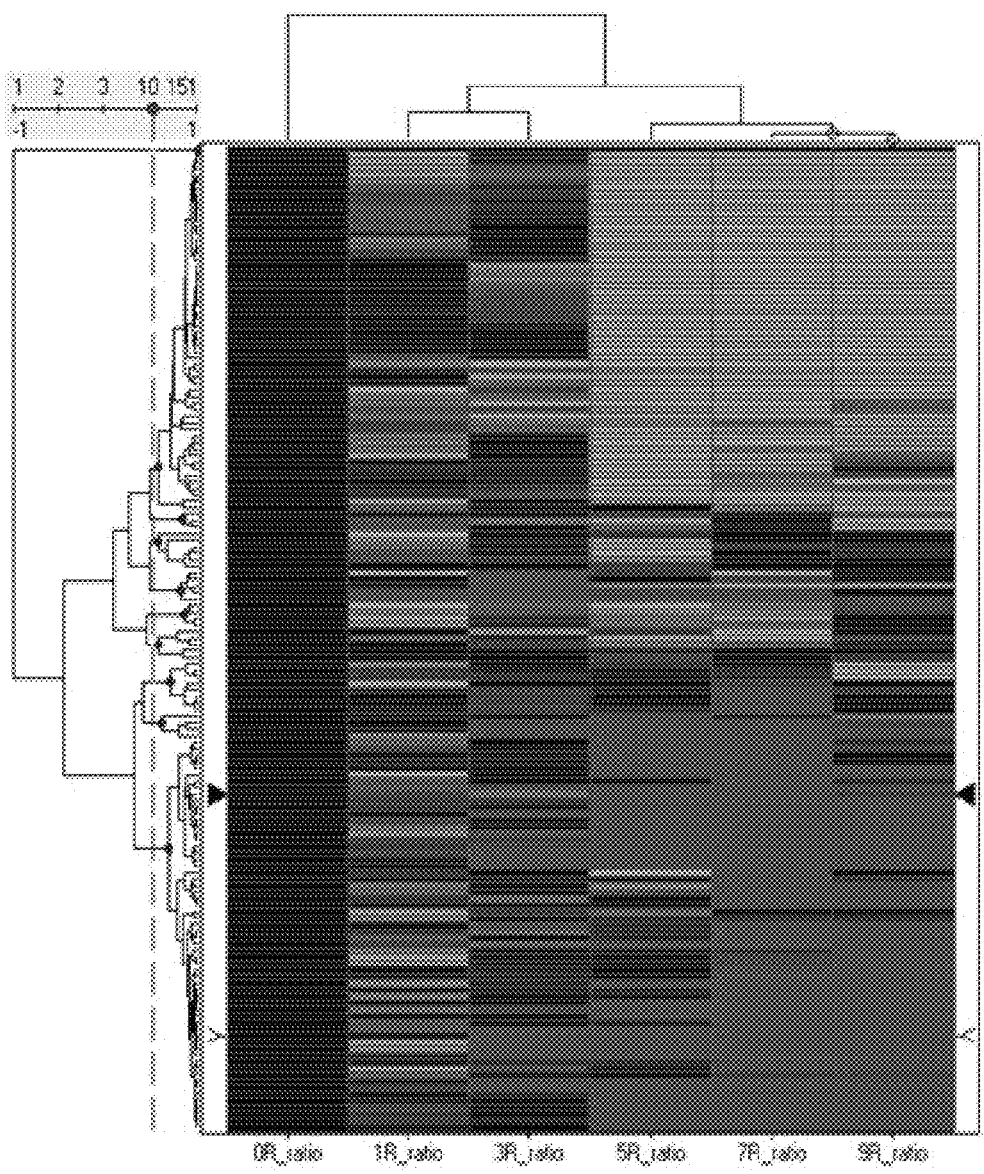

Considerable changes in secondary metabolites were observed and illustrated by overlapping chromatograms of infected and control plant roots at 7 DPI (FIG. 4, Table 3). The levels of most secondary metabolites changed (either increased or decreased) more than 2 fold upon fungal infection as illustrated in the HCA analyses (FIG. 7). Most glycosylated flavonoids and isoflavonoids including apigenin-7-O-glucoside, apigenin-7-O-glucuronide, formononetin-7-O-glucoside (ononin), naringenin-7-o-glucoside and 7,4'-dihydroxyflavone-7-o-glucuronide decreased as much as 20-fold upon fungal infection (Table 3). Molecules were profiled with UPLC/MS and identified according to retention time (R.T.) and MS/ESI spectra and/or comparing with authentic samples. Each molecule was quantified with in-house custom software Met-IDEA and was based on the intensity of characteristic ions relative to the internal standard umbelliferone. The kinetic data was represented with the ratio of metabolite level from 0 to 9 days post inoculation (DPI) with *P. omnivora*.

TABLE 3

Temporal changes in plant secondary metabolites accumulated in *M. truncatula* root inoculated with and without *P. omnivora* at different time points. The temporal changes are represented as relative ratios (control relative to inoculated) for each metabolite from 0 to 9 days post inoculation (DPI) with *P. omnivora*.

| molecules | R.T. | ion | 0DPI_ratio | 1DPI_ratio | 3DPI_ratio | 5DPI_ratio | 7DPI_ratio | 9DPI_ratio |
|---|---|---|---|---|---|---|---|---|
| Naringenin-O-glucoside | 4.048 | 433 | 1 | 0.746444 | 1.007499 | 0.238253 | 0.137898 | 0.027935 |
| 7,4'-hydroxyflavone-7-beta-O-glucuronoside | 4.192 | 253 | 1 | 0.57614 | 2.699832 | 0.152287 | 0.070891 | 0.01735 |
| Apigenin-diglucoside | 4.96 | 269 | 1 | 0.928741 | 0.89219 | 2.031732 | 2.200639 | 1.067115 |
| unknown isoflavone glucoside | 5.5093 | 561 | 1 | 0.913774 | 0.810792 | 0.153579 | 0.078217 | 0.051866 |
| genistin | 6.1227 | 269 | 1 | 0.650103 | 0.525085 | 0.389675 | 0.146649 | 0.058091 |
| unknown isoflavone | 6.176 | 593 | 1 | 1.110618 | 0.709519 | 0.160016 | 0.127548 | 0.128667 |
| Apigenin-7-O-glucuroside | 6.2773 | 445 | 1 | 1.124263 | 0.754646 | 0.195059 | 0.026353 | 0.017065 |
| Naringenin-7-O-glucoside | 6.5866 | 433 | 1 | 0.995172 | 1.304516 | 1.984409 | 2.640729 | 1.32526 |
| Apigenin-7-O-glucoside | 6.7893 | 431 | 1 | 0.721361 | 0.907275 | 0.987827 | 0.661638 | 0.524855 |
| unknown flavonoid glucoside | 6.832 | 629 | 1 | 0.561922 | 0.697793 | 0.106269 | 0.050147 | 0.053303 |
| unknown isoflavonoid glucuroside | 6.8587 | 299 | 1 | 1.031653 | 0.639196 | 0.082314 | 0.053175 | 0.047141 |
| 6,7,4'-trihydroxy-7-isoflavone | 6.8747 | 269 | 1 | 1.300534 | 1.297153 | 1.926142 | 1.433609 | 0.653602 |
| 5,7-OH,4'-methoxyflavone | 7.2107 | 283 | 1 | 0.689251 | 1.138442 | 2.012896 | 6.565541 | 4.388477 |
| 7,4'-hydroxyflavone | 7.568 | 253 | 1 | 0.826145 | 1.724652 | 3.351878 | 5.375823 | 4.543109 |
| Liquiritigenin | 7.8773 | 255 | 1 | 0.770456 | 3.451512 | 5.18792 | 7.413752 | 5.376135 |
| Daidzein | 7.9467 | 253 | 1 | 0.969474 | 3.920644 | 1.051881 | 1.869799 | 1.309809 |
| Formononetin-7-O-glucoside (ononin) | 8.4267 | 267 | 1 | 0.663561 | 1.149542 | 0.184543 | 0.076783 | 0.048267 |
| unknown flavone | 9.376 | 269 | 1 | 0.662436 | 1.244784 | 7.208046 | 12.49505 | 9.535804 |
| unknown isoflavone | 9.744 | 267 | 1 | 0.45977 | 0.899087 | 0.177154 | 0.04026 | 0.029838 |
| Naringenin | 9.7493 | 271 | 1 | 1.102412 | 2.065653 | 5.545646 | 9.001147 | 6.402019 |
| Apigenin | 10.112 | 269 | 1 | 0.797668 | 1.243621 | 4.96945 | 7.47087 | 6.86798 |
| Naringenin chalcone | 10.272 | 271 | 1 | 0.404748 | 0.747852 | 1.233352 | 5.519534 | 5.114527 |
| Medicarpin | 11.1253 | 254 | 1 | 0.676983 | 1.069981 | 0.280647 | 0.09875 | 0.054899 |
| Isoliquiritigenin | 11.664 | 255 | 1 | 1.169655 | 6.425426 | 8.02138 | 8.729333 | 7.129881 |
| Formononetin | 12.4373 | 252 | 1 | 0.475391 | 1.066604 | 0.558171 | 0.179935 | 0.090166 |

Four common precursors of flavones and isoflavones were marginally detected in the control plant roots. However, obvious increased accumulation of all 4 molecules was observed upon fungal infection. At 3 DPI, levels of isoliquiritigenin and liquiritigenin chalcones increased 6 and 3-fold, respectively, relative to control plants and reached a maximum at 7 DPI. The accumulation patterns of naringenin chalcone and naringenin were similar to those of their corresponding 6-deoxy derivatives above, in that marginal levels were detected early and increased to a maximum at 7 DPI in the infected plant roots.

*M. truncatula* roots constitutively accumulate significant levels of isoflavonoids, especially formononetin, and medicarpin. However, increased accumulation of medicarpin, which is widely believed to be the predominant phytoalexin in *Medicago*, was not observed in response to *P. omnivora*. On the contrary, medicarpin levels decreased up to 20-fold by 9 DPI. The accumulation of medicarpin's biosynthetic precursor, formononetin, also decreased by 2, 6 and 10-fold lower at 5, 7 and 9 DPI.

The biosynthesis of other flavonoids was also examined. A 4-fold higher accumulation of apigenin was observed starting at 5 DPI, which increased to more than 6-fold at 7 and 9 DPI. Another interesting flavonoid, 7,4'-dihydroxyflavone also increased substantially by 4-fold at 7 and 9 DPI.

EXAMPLE 7

Genetic Regulation of Flavonoid and Isoflavonoid Pathways

To determine if the decreased levels of medicarpin were due to suppression of the biosynthetic pathway or catabolic detoxification of the metabolite by the fungus, qRT-PCR analysis of the major isoflavonoid and flavonoid pathway genes was performed. Dramatic increases were observed for CHS, CHR and CHI, the common upstream genes to both pathways, between 5 and 9 DPI (FIG. 3). CHS levels progressively increased by 77-fold at 9 DPI and CHR increased by 37-fold at 9 days. Similarly, flavone synthase (FS) was induced dramatically by 83-fold at 7 DPI following *P. omnivora* infection. To the contrary, isoflavonoid biosynthesis genes such as isoflavone synthase (IFS) expression decreased by a 3-fold at 9 DPI. Compared to other genes, the induction of IFS was more moderate and not competitive to direct carbon flux into this pathway. The levels of vestitone reductase (VR), which converts vestitone to medicarpin, increased modestly with a maximum of 4-fold a 5 DPI.

EXAMPLE 8

Fungal Inhibition Assay

Many natural products have anti-fungal activity and those compounds yielding differential accumulation in the metabolite profiling experiments were tested for in vitro anti-fungal activity against *P. omnivora*. A semi-quantitative fungal inhibition activity assay was a modified from a previous report (Blount et al., 1992) as the hyphae of *P. omnivora* extend randomly on the PDA medium. Fungal growth inhibition was assayed on PDA medium for 5 days. Compounds tested were pre-dissolved in DMSO to make 25 mM and 5 mM stock solutions, which were then diluted to 1 mL with PDA medium to yield final concentrations of 0.5 mM and 0.1 mM for inhibition assay. A 2 mm fungal plug was then incubated in the prepared assay solutions and fungal growth was recorded under a microscope every 12 h up to 48 h. For each assayed molecule, the fungal growth was recorded using an arbitrary scale from 0 to 5 with 0 as no fungal growth (i.e. maximum inhibition) and 5 as the best fungal growth (i.e. minimum inhibition) by comparing with the medium plus DMSO (20 µL in 1 mL PDA) blank. Catechol (at concentration of 10 mM) was used as positive control and formononetin, which bears no antifungal activity, was used as negative control. All experiments were replicated four times.

Figure 5:
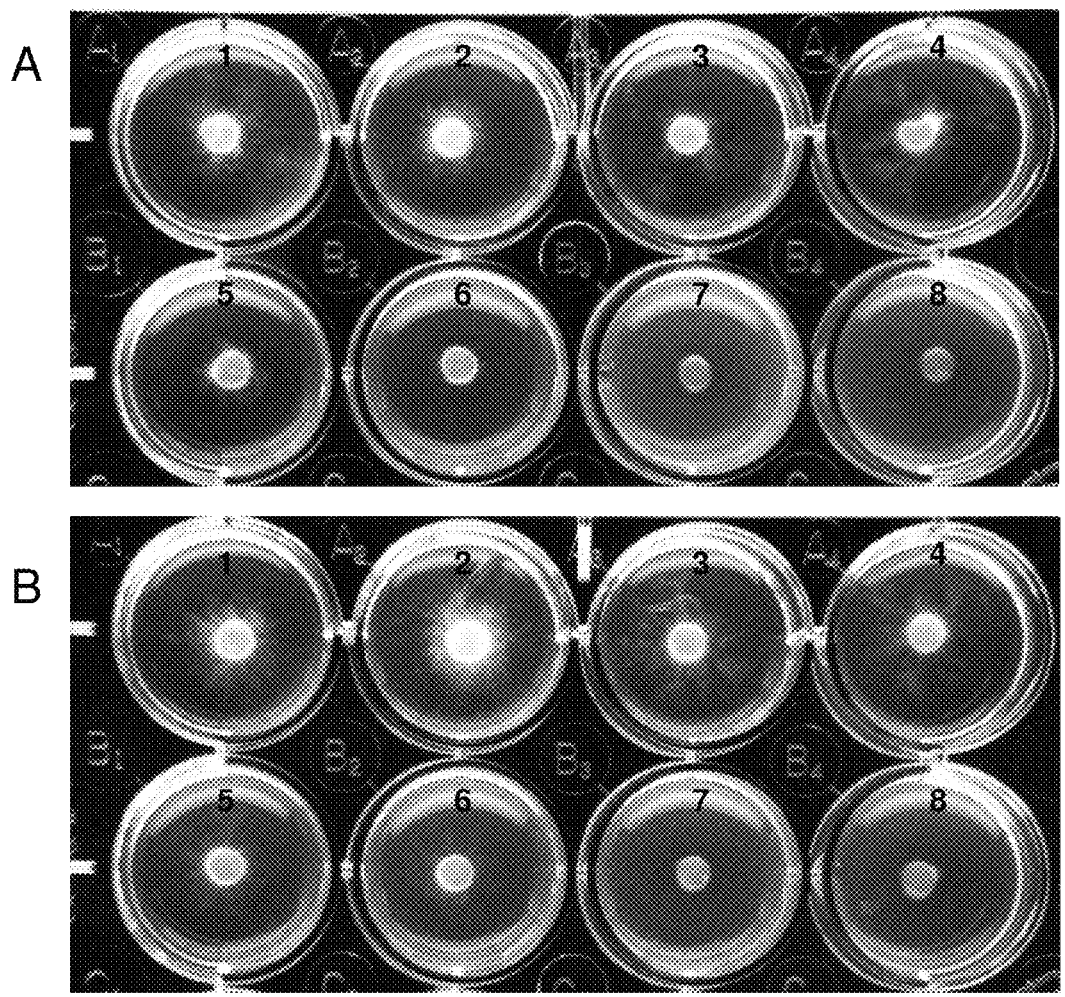
FIG. 5. *P. omnivora* growth was inhibited by medicarpin and 7,4'-dihydroxyflavone. Fungal inhibition assay 120 h with medicarpin (A) and 7,4'-dihydroxyflavone (B). 1, 2, control; 3, 4, DMSO control; 5, 6, compound concentration at 0.1 mM; 7, 8, compound concentration at 0.5 mM.

Fungal growth was scored using an arbitrary 0 to 5 scale with the best fungal growth (which indicates no inhibition) assigned to 5 and no fungal growth (which indicates best inhibition) to 0 (Table 4; FIG. 5).

TABLE 4

Fungal inhibition assay against *P. omnivora* (120 h).

| Compounds | control | | DMSO | | 0.1 mM | | 0.5 mM | |
|---|---|---|---|---|---|---|---|---|
| catechol | 5 | 5 | 5 | 5 | 2 | 2 | 0 | 0 |
| formononetin | 5 | 5 | 4 | 4 | 4 | 4 | 4 | 4 |
| naringenin | 4 | 5 | 4 | 4 | 4 | 5 | 3 | 5 |
| liquiritigenin | 5 | 5 | 5 | 5 | 5 | 5 | 5 | 5 |
| isoliquiritigenin | 5 | 5 | 5 | 5 | 4 | 4 | 4 | 4 |
| apigenin | 4 | 4 | 4 | 4 | 5 | 5 | 5 | 5 |
| medicarpin | 5 | 5 | 4 | 4 | 2 | 1 | 1 | 0 |
| 7,4'-dihydroxyflavone | 5 | 5 | 5 | 5 | 3 | 3 | 0 | 0 |

The common precursors of the flavonoid and isoflavonoid pathways including naringenin, liquiritigenin and their corresponding chalcones showed no inhibition activity against the fungus. The pterocarpan medicarpin possessed strong inhibition, but its isoflavonoid precursor, formononetin was not active. The flavonoids apigenin and 6,7,4'-trihydoxyflavone were not active. However, 7,4'-dihydroxyflavone, which was induced in plant roots upon fungal infection, strongly inhibited *P. omnivora* growth.

REFERENCES

The references listed below are incorporated herein by reference to the extent that they supplement, explain, provide a background for, or teach methodology, techniques, and/or compositions employed herein.

U.S. Pat. No. 4,518,584; U.S. Pat. No. 4,535,060; U.S. Pat. No. 4,737,462; U.S. Pat. No. 5,302,523; U.S. Pat. No. 5,322,783; U.S. Pat. No. 5,384,253; U.S. Pat. No. 5,464,765; U.S. Pat. No. 5,508,184; U.S. Pat. No. 5,508,468; U.S. Pat. No. 5,538,877; U.S. Pat. No. 5,538,880; U.S. Pat. No. 5,550,318; U.S. Pat. No. 5,545,818; U.S. Pat. No. 5,563,055; U.S. Pat. No. 5,591,616; U.S. Pat. No. 5,610,042; U.S. Pat. No. 5,824,872; U.S. Pat. No. 6,072,103; U.S. Pat. No. 7,005,562.

U.S. Patent Application Publication 2005/0257286; U.S. Patent Applic. Publn. 2006/0041950; U.S. Patent Application Publication 2006/0053509.

Abdullah et al., *Biotechnology*, 4:1087, 1986.
Akashi et al, *Pl. Physiol.* 121:821-828, 1999.
Altschuhl et al., *Nucl. Acids Res.* 25:3389-3402, 1997.
Bates, *Mol. Biotechnol.*, 2(2):135-145, 1994.
Battraw and Hall, *Theor. App. Genet.*, 82:161-168, 1991.
Bevan et al., *Nucleic Acids Research*, 11:369-385, 1983.
Bhattacharjee et al., *J. Plant Bioch. and Biotech.*, 6:69-73. 1997.
Blount et al., *Physiol. Molec. Pl. Pathol.* 41:333-349, 1992.
Broeckling et al., *J. Exp. Bot.* 56: 323-336, 2005.
Broeckling et al., *Anal. Chem.* 78:4334-4341, 2006.
Buchanan-Wollaston et al., *Plant Cell Reports,* 11:627-631. 1992

Buising and Benbow, *Mol. Gen. Genet.,* 243:71-81. 1994.
Callis et al., *Genes Dev.,* 1:1183-1200, 1987.
Casa et al., *Proc. Natl. Acad. Sci. USA,* 90:11212-11216, 1993.
Chabaud et al., *Pl. Cell Rep.* 22:46-51, 2003.
Chandler et al., *Plant Cell,* 1:1175-1183, 1989.
Christou; et al., *Proc. Natl. Acad. Sci. USA,* 84:3962-3966, 1987.
Chu et al., *Scientia Sinica,* 18:659-668, 1975.
Conkling et al., *Plant Physiol.,* 93:1203-1211, 1990.
Czechowski et al., *Pl. Physiol.* 139:5-17, 2005.
De Block et al., *EMBO J.,* 6:2513-2518, 1987.
De Block et al., *Plant Physiol.,* 91:694-701, 1989.
Dellaporta et al., In: *Chromosome Structure and Function: Impact of New Concepts,* 18th Stadler Genetics Symposium, 11:263-282, 1988.
D'Halluin et al., *Plant Cell,* 4:1495-1505, 1992.
Dixon, *Nature* 411: 843-847, 2001.
Dixon et al., *Molec. Pl. Pathol.* 3: 371-390, 2002.
Ebert et al., *Proc. Natl. Acad. Sci. USA,* 84:5745-5749, 1987.
European Patent Appln. 154,204.
Farag et al., *Phytochemistry* 68:342-354, 2007.
Farag et al., *Plant Physiol.* 146:387-402, 2008.
Fiehn et al., *Metabolomics* 3:175-178, 2007.
Fraley et al., *Bio/Technology,* 3:629-635, 1985.
Fromm et al., *Nature,* 319:791-793, 1986.
Gallie et al., *Plant Cell,* 1:301-311, 1989.
Gelvin et al., In: *Plant Molecular Biology Manual,* 1990.
Germany Patent Appln. DE 3642 829 A.
Ghosh-Biswas et al., *J. Biotechnol.,* 32:1-10, 1994.
Gomez et al., *BMC Plant Biol.* 9:10, 2009.
Harrison et al, *Plant Cell,* 14: 2413-2429, 2002.
Harrison, *Ann. Rev. Microbiol.* 59: 19-42, 2005.
Haseloff et al., *Proc. Natl. Acad. Sci. USA,* 94:2122-2127, 1997.
He et al., *Plant Cell Reports,* 14:192-196, 1994.
Herrera-Estrella et al, *Nature,* 303:209-213, 1983.
Hiei et al., *Plant. Mol. Biol.,* 35:205-218, 1997.
Hinchee et al., *Bio/technol.,* 6:915-922, 1988.
Hou and Lin, *Plant Physiology,* 111:166, 1996.
Hudspeth and Grula, *Plant Mol. Biol.,* 12:579-589, 1989.
Ikuta et al., *Bio/technol.,* 8:241-242, 1990.
Ishida et al., *Nat. Biotechnol.,* 14:745-750, 1996.
Kaeppler et al., *Plant Cell Reports* 9: 415-418, 1990.
Kaeppler et al., *Theor. Appl. Genet.,* 84:560-566, 1992.
Kakar et al., *Plant Methods* 4:18, 2008.
Katz et al., *J. Gen. Microbiol.,* 129:2703-2714, 1983.
Kessmann et al., *Pl. Physiol.* 94:227-232, 1990.
Klee et al., *Bio-Technology,* 3:637-642, 1985.
Knittel et al., *Plant Cell Reports,* 14(2-3):81-86, 1994.
Kyte and Doolittle, *J. Mol. Biol.,* 157:105 132, 1982.
Lawton et al., *Plant Mol. Biol.* 9:315-324, 1987.
Lazzeri, *Methods Mol. Biol.,* 49:95-106, 1995.
Lee et al., *Korean J. Genet.,* 11:65-72, 1989.
Li et al., *Planta* 226:109-123, 2007.
Lorz et al., *Mol Gen Genet,* 199:178-182, 1985.
Lyda, *Ann. Rev. Phytopathol.* 16:193-209, 1978
Lyda & Kenerley, *Phymatotrichum.* In: Singleton et al., eds. Methods for Research on Soilborne Phytopathogenic Fungi. St. Paul, Minn., USA: American Phytopathological Society Press, p. 145-148, 1992.
Marcotte et al., *Nature,* 335:454, 1988.
Martens and Mithofer, *Phytochemistry* 66:2399-2407, 2005.
McCabe and Martinell, *Bio-Technology,* 11:596-598, 1993.
McCormac et al., *Euphytica,* 99:17-25, 1998.
McKersie et al., *Plant Physiol.* 103:1155-1163, 1993.
Murakami et al., *Mol. Gen. Genet.,* 205:42-50, 1986.
Murashige and Skoog, *Physiol. Plant.,* 15:473-497, 1962.
Nagatani et al., *Biotech. Tech.,* 11:471-473, 1997.
Naoumkina et al., *BMC Plant Biol.* 8:132, 2008.
Odell et al., *Nature,* 313:810-812, 1985.
Ogawa et al., *Sci. Rep.,* 13:42-48, 1973.
Omirulleh et al., *Plant Mol. Biol.,* 21:415-428, 1993.
Ow et al., *Science,* 234:856-859, 1986.
PCT Appln. WO 9217598; PCT Appln. WO 94/09699; PCT Appln. WO 95/06128; PCT Appln. WO 97/4103; PCT Appln. WO 97/41228; PCT Appln. WO 00/65073; PCT Appln. WO 01/053502.
Pfaffl, *Nucleic Acids Res.* 29: e45, 2001.
Pontier et al., *Plant J.* 5: 507-521, 1994.
Potrykus et al., *Mol. Gen. Genet.,* 199:183-188, 1985.
Prasher et al., *Biochem. Biophys. Res. Commun.,* 126:1259-1268, 1985.
Ramakers et al, *Neuroscience Letters* 339:62-66, 2003.
Reichel et al., *Proc. Natl. Acad. Sci. USA,* 93:5888-5893, 1996.
Rhodes et al., *Methods Mol. Biol.,* 55:121-131, 1995.
Ritala et al., *Plant Mol. Biol.,* 24:317-325, 1994.
Rogers et al., *Methods Enzymol.,* 153:253-277, 1987.
Samac et al., *Transgenic Res.* 13:349-361, 2004.
Sambrook et al., In: *Molecular Cloning—A Laboratory Manual* (second edition), Cold Spring Harbour Laboratory Press, 1989.
Saunders and O'Neill, *Biocontrol* 49: 715-728, 2005.
Schliemann et al., *Phytochemistry* 69:112-146, 2008.
Sheen et al., *Plant Journal,* 8:777-784, 1995.
Singsit et al., *Transgenic Res.,* 6:169-176, 1997.
Stalker et al., *Science,* 242:419-422, 1988.
Stein, *J Am Soc Mass Spectrom* 10:770-781, 1999.
Streets and Bloss, *Am. Phytopathol. Soc. Monogr.* 8:1-38, 1973.
Sullivan et al., *Mol. Gen. Genet.,* 215:431-440, 1989.
Sumner et al., *Phytochemistry* 62: 817-836, 2003.
Sumner et al., *Metabolomics* 3:211-221, 2007.
Sutcliffe, *Proc. Natl. Acad. Sci. USA,* 75:3737-3741, 1978.
Suzuki et al., *Planta,* 220:696-707, 2005.
Thillet et al., *J. Biol. Chem.,* 263:12500-12508, 1988.
Thomas et al., *Plant Sci.,* 69:189-198, 1990.
Thompson et al., *EMBO J.,* 6:2519-2523, 1987.
Thompson et al., *Nucleic Acids Res* 25: 4876-4882, 1995.
Tian et al., *Plant Cell Rep.,* 16:267-271, 1997.
Tingay et al., *Plant J.,* 11:1369-1376, 1997.
Tomes et al., *Plant. Mol. Biol.* 14:261-268, 1990.
Toriyama et al., *Theor Appl. Genet.,* 73:16, 1986.
Tsukada et al., *Plant Cell Physiol.,* 30: 599-604, 1989.
Twell et al., *Plant Physiol* 91:1270-1274, 1989.
Uchimiya et al., *Mol. Gen. Genet.,* 204:204, 1986.
Van Eck et al., *Plant Cell Reports,* 14:299-304, 1995.
Vasil et al., *Plant Physiol.,* 91:1575-1579, 1989.
Walder et al., *Gene,* 42:133, 1986.
Walker et al., *Proc. Natl. Acad. Sci. USA,* 84:6624-6628, 1987.
Wang et al., *Molecular and Cellular Biology,* 12:3399-3406, 1992.
Weber et al., *Plant Cell* 11: 485-494, 1999.
Yamada et al., *Plant Cell Rep.,* 4:85, 1986.
Yamamoto et al., *Pl. Cell* 3:371-382, 1991.
Yang and Russell, *Proc. Natl. Acad. Sci. USA,* 87:4144-4148, 1990.
Zhang et al., *Pl. Physiol.* 144:741-751, 2007.
Zhang et al., *Plant J.* 57: 171-183, 2009.
Zheng and Edwards, *J. Gen. Virol.,* 71:1865-1868, 1990.
Zhou et al., *Plant Cell Reports,* 12: 612-616, 1993.
Zukowsky et al., *Proc. Natl. Acad. Sci. USA,* 80:1101-1105, 1983.

What is claimed is:

1. A transgenic legume plant comprising a heterologous nucleic acid sequence that increases expression of flavone synthase or isoflavone synthase, wherein synthesis of medicarpin or 7,4'-dihydroxyflavone is up-regulated in the roots of the plant relative to an otherwise identical plant not comprising the heterologous nucleic acid sequence, wherein expression of the heterologous nucleic acid sequence is up-regulated in response to infection by a fungal plant pathogen or a fungal mutualist, wherein the heterologous nucleic acid sequence comprises a promoter selected from the group consisting of root-preferred promoter and fungal-inducible promoter, wherein the promoter is operably linked to a sequence selected from the group consisting of:
   a) a nucleic acid sequence encoding the polypeptide of SEQ ID NO:4, SEQ ID NO:5, SEQ ID NO:7, or SEQ ID NO:9;
   b) a nucleic acid sequence comprising the sequence of SEQ ID NO:3; SEQ ID NO:6, or SEQ ID NO:8;
   c) a nucleic acid sequence having at least 98% sequence identity to the nucleic acid sequence of SEQ ID NO:3; SEQ ID NO:6, or SEQ ID NO:8 and which encodes a polypeptide having flavone synthase or isoflavone synthase activity; and
   d) a nucleic acid sequence encoding a polypeptide having at least 90% sequence identity to SEQ ID NO:4, SEQ ID NO:5, SEQ ID NO:7, or SEQ ID NO:9 and having flavone synthase or isoflavone synthase activity.

2. The plant of claim 1, wherein the fungal-inducible promoter is an hsr203J, PVS3, NI16, MtPT4, or STS8 stilbene synthase promoter.

3. The plant of claim 1, wherein the fungal plant pathogen is *Phymatotrichopsis omnivora*.

4. The plant of claim 1, wherein the plant exhibits increased resistance to *Phymatotrichopsis omnivora* relative to an otherwise identical plant not comprising the heterologous nucleic acid sequence.

5. The plant of claim 1, wherein the plant is alfalfa.

6. The plant of claim 1, wherein the heterologous nucleic acid sequence is expressed in root tissue.

7. The plant of claim 6, wherein the promoter is a root-preferred promoter.

8. The plant of claim 7, wherein the root-preferred promoter is an RB7, RPE15, RPE14, RPE19, RPE29, RPE60, RPE2, RPE39, RPE61, SHR, ELG3, EXP7, EXP18 or At1g73160 promoter.

9. The plant of claim 1, wherein accumulation of 7,4-dihydroxyflavone and/or medicarpin occurs prior to contacting the plant with *Phymatotrichopsis omnivora*.

10. The plant of claim 1, wherein accumulation of 7,4-dihydroxyflavone or medicarpin occurs subsequent to the plant's contact with *Phymatotrichopsis omnivora*.

11. Seed of the plant of claim 1, comprising the heterologous nucleic acid sequence.

12. A plant cell of the plant of claim 1, comprising the heterologous nucleic acid sequence.

13. A method of producing a legume plant with increased resistance to *Phymatotrichopsis omnivora*, the method comprising: expressing in the legume plant the heterologous nucleic acid sequence of claim 1 encoding flavone synthase or isoflavone synthase that increases accumulation of medicarpin or 7,4'-dihydroxyflavone in the roots of the plant, relative to an otherwise similar plant not comprising the heterologous nucleic acid sequence.

14. The method of claim 13, wherein the heterologous nucleic acid sequence encoding flavone synthase or isoflavone synthase is operably linked to an inducible promoter.

15. The method of claim 13, wherein the fungal plant pathogen or a fungal mutualist is *Phymatotrichopsis omnivora*.

16. The method of claim 15, wherein up-regulation is through a fungal-inducible promoter, wherein the fungal pathogen-inducible promoter is an hsr203J, PVS3, NI16, or STS8 stilbene synthase promoter.

17. The method of claim 13, wherein the heterologous nucleic acid sequence is transformed into a legume plant and progeny of the legume plant are grown such that a modified legume plant is produced that is homozygous for the heterologous nucleic acid sequence.

18. The method of claim 13, wherein the plant is alfalfa.

19. A method of obtaining a legume plant that is not susceptible to *Phymatotrichopsis* Root Rot in soil that comprises *Phymatotrichopsis omnivora*, the method comprising:
   (a) expressing the one or more heterologous nucleic acid sequence(s) of claim 1 in the legume plant that up-regulates the synthesis of medicarpin or 7,4'-dihydroxyflavone in roots of the plant relative to an otherwise identical plant not comprising the heterologous nucleic acid sequence(s), and
   (b) selecting a plant expressing the one or more heterologous nucleic acid sequence(s).

20. The method of claim 19, further comprising:
   (c) analyzing the plant for infection by *P. omnivora*.

21. The method of claim 19, wherein the heterologous nucleic acid sequence is transformed into a legume plant of the variety and progeny of the legume plant are grown such that a modified legume plant is produced that is homozygous for the heterologous nucleic acid sequence.

22. The method of claim 19, wherein the heterologous nucleic acid sequence is expressed in the roots of the plant.

23. The method of claim 19, wherein the heterologous nucleic acid sequence is expressed in response to infection by a root-infecting fungal plant pathogen.

24. The method of claim 19, wherein the plant is alfalfa.

* * * * *

SEQUENCE LISTING

<160> NUMBER OF SEQ ID NOS: 23

<210> SEQ ID NO 1
<211> LENGTH: 1572
<212> TYPE: DNA
<213> ORGANISM: Glycyrrhiza echinata

<400> SEQUENCE: 1

| | | | | | |
|---|---|---|---|---|---|
| atgttggtgg | aacttgcaat | tactctgttg | gtgatagccc | tgttcataca | cctgcgtccc | 60 |
| acactaagtg | caaaatcaaa | gtcccttcgc | cacctcccaa | accctccaag | tccaaaaccc | 120 |
| cgtctcccat | ttgtgggtca | ccttcacctt | ttagacaaac | cccttctcca | ctactccctc | 180 |
| atcgacctaa | gcaaacgcta | tggtccgctt | tactccctct | acttcggttc | catgccaacc | 240 |
| gttgtagcct | ccacccctga | acttttcaaa | ctcttcctcc | aaactcacga | ggcctcttcc | 300 |
| ttcaacacaa | ggttccaaac | tctctgccatt | aggcgcctaa | cctacgacaa | ctctgttgcc | 360 |
| atggttccct | ttggtcctta | ctggaagttc | attaggaagc | tcatcatgaa | cgacctcctc | 420 |
| aatgccacaa | ctgtgaacaa | gttgaggcct | taaggagcc | agaaatccg | aaaggtcctc | 480 |
| agggtgatgg | cacagagtgc | tgagtctcag | gtcccactta | atgtcaccga | ggagcttctc | 540 |
| aagtggacca | acagcaccat | ctcgaggatg | atgcttgggg | aagcagagga | aatcagggac | 600 |
| atagcacgtg | acgtgcttaa | gatctttggg | gagtatagtc | tcaccgactt | catctggccc | 660 |
| ttgaagaaac | tcaaggttgg | gcaatacgag | aagaggattg | acgatatatt | caacaggttt | 720 |
| gaccccgtca | ttgagagggt | catcaagaaa | agacaggaga | ttaggaagaa | gaggaaggag | 780 |
| aggaatggtg | agatcgagga | gggtgaacag | agtgtggttt | ttctcgacac | tttgctcgat | 840 |
| tttgctgagg | acgagaccat | ggagatcaaa | atcaccaagg | aacaaatcaa | gggccttgtt | 900 |
| gtggatttct | tctcagcagg | gacggattcc | acggcggtgg | caacagactg | ggctctgtca | 960 |
| gagctcatca | acaaccccag | ggtgtttcaa | aaggcacgag | aggagatcga | tgccgtcgtg | 1020 |
| ggaaaagaca | gactcgttga | cgaggcagat | gtccagaacc | ttccttacat | tagatccatc | 1080 |
| gtgaaggaga | cgttccgcat | gcacccacca | ctacccgtgg | tcaaaagaaa | gtgcgtgcag | 1140 |
| gagtgtgagg | tcgacggtta | tgtgatccca | gagggagcat | tgatcctttt | caatgtttgg | 1200 |
| gccgtcggaa | gagacccaaa | atactgggac | aggcccactg | agttccgtcc | cgaaaggttc | 1260 |
| ttagaaaatg | tgggtgaagg | ggatcaagcc | gttgaccta | ggggtcaaca | tttccaactt | 1320 |
| cttccgtttg | ggtctggaag | gaggatgtgc | cctggcgtca | atttggccac | tgcgggaatg | 1380 |
| gccacactgc | ttgcgtcagt | tatccagtgc | tttgatctca | gcgtagtggg | cccacaggga | 1440 |
| aagatattga | aggcaatga | tgccaaggtt | agcatggaag | agagagctgg | actcacggtt | 1500 |
| ccaagggcac | ataacctcat | ctgtgtcccg | gttgcaagat | caagtgccgt | acccaaactc | 1560 |
| ttttcgtcgt | aa | | | | | 1572 |

<210> SEQ ID NO 2
<211> LENGTH: 523
<212> TYPE: PRT
<213> ORGANISM: Glycyrrhiza echinata

<400> SEQUENCE: 2

Met Leu Val Glu Leu Ala Ile Thr Leu Leu Val Ile Ala Leu Phe Ile
1               5                   10                  15

His Leu Arg Pro Thr Leu Ser Ala Lys Ser Lys Ser Leu Arg His Leu
            20                  25                  30

Pro Asn Pro Pro Ser Pro Lys Pro Arg Leu Pro Phe Val Gly His Leu

```
                35                  40                  45
His Leu Leu Asp Lys Pro Leu His Tyr Ser Leu Ile Asp Leu Ser
 50                  55                  60

Lys Arg Tyr Gly Pro Leu Tyr Ser Leu Tyr Phe Gly Ser Met Pro Thr
 65                  70                  75                  80

Val Val Ala Ser Thr Pro Glu Leu Phe Lys Leu Phe Leu Gln Thr His
                 85                  90                  95

Glu Ala Ser Ser Phe Asn Thr Arg Phe Gln Thr Ser Ala Ile Arg Arg
                100                 105                 110

Leu Thr Tyr Asp Asn Ser Val Ala Met Val Pro Phe Gly Pro Tyr Trp
                115                 120                 125

Lys Phe Ile Arg Lys Leu Ile Met Asn Asp Leu Leu Asn Ala Thr Thr
                130                 135                 140

Val Asn Lys Leu Arg Pro Leu Arg Ser Gln Ile Arg Lys Val Leu
145                 150                 155                 160

Arg Val Met Ala Gln Ser Ala Glu Ser Gln Val Pro Leu Asn Val Thr
                165                 170                 175

Glu Glu Leu Leu Lys Trp Thr Asn Ser Thr Ile Ser Arg Met Met Leu
                180                 185                 190

Gly Glu Ala Glu Glu Ile Arg Asp Ile Ala Arg Asp Val Leu Lys Ile
                195                 200                 205

Phe Gly Glu Tyr Ser Leu Thr Asp Phe Ile Trp Pro Leu Lys Lys Leu
                210                 215                 220

Lys Val Gly Gln Tyr Glu Lys Arg Ile Asp Asp Ile Phe Asn Arg Phe
225                 230                 235                 240

Asp Pro Val Ile Glu Arg Val Ile Lys Lys Arg Gln Glu Ile Arg Lys
                245                 250                 255

Lys Arg Lys Glu Arg Asn Gly Glu Ile Glu Gly Glu Gln Ser Val
                260                 265                 270

Val Phe Leu Asp Thr Leu Leu Asp Phe Ala Glu Asp Glu Thr Met Glu
                275                 280                 285

Ile Lys Ile Thr Lys Glu Gln Ile Lys Gly Leu Val Val Asp Phe Phe
                290                 295                 300

Ser Ala Gly Thr Asp Ser Thr Ala Val Ala Thr Asp Trp Ala Leu Ser
305                 310                 315                 320

Glu Leu Ile Asn Asn Pro Arg Val Phe Gln Lys Ala Arg Glu Glu Ile
                325                 330                 335

Asp Ala Val Val Gly Lys Asp Arg Leu Val Asp Glu Ala Asp Val Gln
                340                 345                 350

Asn Leu Pro Tyr Ile Arg Ser Ile Val Lys Glu Thr Phe Arg Met His
                355                 360                 365

Pro Pro Leu Pro Val Val Lys Arg Lys Cys Val Gln Glu Cys Glu Val
                370                 375                 380

Asp Gly Tyr Val Ile Pro Glu Gly Ala Leu Ile Leu Phe Asn Val Trp
385                 390                 395                 400

Ala Val Gly Arg Asp Pro Lys Tyr Trp Asp Arg Pro Thr Glu Phe Arg
                405                 410                 415

Pro Glu Arg Phe Leu Glu Asn Val Gly Glu Gly Asp Gln Ala Val Asp
                420                 425                 430

Leu Arg Gly Gln His Phe Gln Leu Leu Pro Phe Gly Ser Gly Arg Arg
                435                 440                 445

Met Cys Pro Gly Val Asn Leu Ala Thr Ala Gly Met Ala Thr Leu Leu
450                 455                 460
```

```
Ala Ser Val Ile Gln Cys Phe Asp Leu Ser Val Val Gly Pro Gln Gly
465                 470                 475                 480

Lys Ile Leu Lys Gly Asn Asp Ala Lys Val Ser Met Glu Glu Arg Ala
                485                 490                 495

Gly Leu Thr Val Pro Arg Ala His Asn Leu Ile Cys Val Pro Val Ala
            500                 505                 510

Arg Ser Ser Ala Val Pro Lys Leu Phe Ser Ser
        515                 520

<210> SEQ ID NO 3
<211> LENGTH: 1572
<212> TYPE: DNA
<213> ORGANISM: Medicago truncatula

<400> SEQUENCE: 3
atgttggtgg aacttgcagt tactttattg gtgattgctc tttttataca cttacgtcca     60
acacctactg caaaatcaaa ggcacttcgc catcttccaa atccaccaag ccctaaacca    120
cgtcttcctt tcattggtca tcttcatctt ttggataacc cacttcttca ccacactctt    180
atcaagttag gaaagcgtta tggacctttg tacactcttt actttggttc catgcctacc    240
gttgttgcat ccactcctga cttgtttaaa cttttccttc aaacccatga agctacttcc    300
tttaacacaa gattccaaac tctgctatt agtcgtctta cctatgataa ttctgttgct    360
atggttccat ttgcacctta ttggaagttt attagaaagc ttatcatgaa cgacttgctc    420
aacgccacca ctgttaacaa attgaggcca ttgaggagcc gagaaatcct taaggttctt    480
aaggtcatgg ctaatagtgc tgaaactcaa cagccacttg atgtcactga ggagcttctc    540
aagtggacaa acagcacaat ctctaccatg atgttgggtg aggccgaaga ggttagagat    600
attgctcgtg atgttcttaa gatctttgga gaatatagtg ttacaaactt tatttggcct    660
ttgaacaagt ttaagtttgg aaactatgat aagagaactg aggagatttt caataagtat    720
gatcctatca ttgaaaaggt tatcaagaaa cgacaagaga ttgtgaacaa agaaaaaat    780
ggagaaatcg tagagggcga gcagaatgtt gttttcttg acactttgct tgaatttgca    840
caagatgaga ccatggagat caaaattaca aaggaacaaa tcaagggtct tgttgtggat    900
ttcttctctg cagggacaga ttccacagct gtggcaacag aatggacttt ggcagagctc    960
atcaacaatc aagagtatg gaagaaagca caagaagaga ttgactctgt tgtgggaaaa   1020
gatagactag ttgacgaatc agatgttcag aatcttccat acattcgcgc catggtgaag   1080
gaggtattcc gtttgcaccc accactaccc gtggtgaaga gaaatgcac cgaagagtgt   1140
gagatcaatg gttatgtgat cccggaggga gctttgatac ttttcaatgt atggcaagtg   1200
ggaagagacc caaatattg gaaaaaacca ttggaatttc gtccagagag gttcttagaa   1260
aatgcaagcc aaggtgaagg tgaagcagct tcaattgatc ttaggggtca acatttcaca   1320
cttctaccat ttgggtctgg aagaaggatg tgtcctggag tcaatttggc aacagcagga   1380
atggcaacac tactttcatc aattattcag tgttttgatc tacaagtacc aggcccacat   1440
ggacaaatat tgaaaggtga tgatgttaag gttagcatgg atgagagacc tggtcttacg   1500
gttccaagag cacataatct catgtgtgtt ccacttgcaa gagctggtgt tgctgctaaa   1560
ctcctttcct ga                                                       1572

<210> SEQ ID NO 4
<211> LENGTH: 523
<212> TYPE: PRT
```

<213> ORGANISM: Medicago truncatula

<400> SEQUENCE: 4

Met Leu Val Glu Leu Ala Val Thr Leu Leu Val Ile Ala Leu Phe Ile
1               5                   10                  15

His Leu Arg Pro Thr Pro Thr Ala Lys Ser Lys Ala Leu Arg His Leu
            20                  25                  30

Pro Asn Pro Ser Pro Lys Pro Arg Leu Pro Phe Ile Gly His Leu
        35                  40                  45

His Leu Leu Asp Asn Pro Leu Leu His His Thr Leu Ile Lys Leu Gly
    50                  55                  60

Lys Arg Tyr Gly Pro Leu Tyr Thr Leu Tyr Phe Gly Ser Met Pro Thr
65              70                  75                  80

Val Val Ala Ser Thr Pro Asp Leu Phe Lys Leu Phe Leu Gln Thr His
                85                  90                  95

Glu Ala Thr Ser Phe Asn Thr Arg Phe Gln Thr Ser Ala Ile Ser Arg
            100                 105                 110

Leu Thr Tyr Asp Asn Ser Val Ala Met Val Pro Phe Ala Pro Tyr Trp
        115                 120                 125

Lys Phe Ile Arg Lys Leu Ile Met Asn Asp Leu Leu Asn Ala Thr Thr
130                 135                 140

Val Asn Lys Leu Arg Pro Leu Arg Ser Arg Glu Ile Leu Lys Val Leu
145                 150                 155                 160

Lys Val Met Ala Asn Ser Ala Glu Thr Gln Gln Pro Leu Asp Val Thr
                165                 170                 175

Glu Glu Leu Leu Lys Trp Thr Asn Ser Thr Ile Ser Thr Met Met Leu
            180                 185                 190

Gly Glu Ala Glu Glu Val Arg Asp Ile Ala Arg Asp Val Leu Lys Ile
        195                 200                 205

Phe Gly Glu Tyr Ser Val Thr Asn Phe Ile Trp Pro Leu Asn Lys Phe
210                 215                 220

Lys Phe Gly Asn Tyr Asp Lys Arg Thr Glu Glu Ile Phe Asn Lys Tyr
225                 230                 235                 240

Asp Pro Ile Ile Glu Lys Val Ile Lys Arg Gln Glu Ile Val Asn
                245                 250                 255

Lys Arg Lys Asn Gly Glu Ile Val Glu Gly Gln Asn Val Val Phe
            260                 265                 270

Leu Asp Thr Leu Leu Glu Phe Ala Gln Asp Glu Thr Met Glu Ile Lys
        275                 280                 285

Ile Thr Lys Glu Gln Ile Lys Gly Leu Val Val Asp Phe Phe Ser Ala
290                 295                 300

Gly Thr Asp Ser Thr Ala Val Ala Thr Glu Trp Thr Leu Ala Glu Leu
305                 310                 315                 320

Ile Asn Asn Pro Arg Val Trp Lys Lys Ala Gln Glu Glu Ile Asp Ser
                325                 330                 335

Val Val Gly Lys Asp Arg Leu Val Asp Glu Ser Asp Val Gln Asn Leu
            340                 345                 350

Pro Tyr Ile Arg Ala Met Val Lys Glu Val Phe Arg Leu His Pro Pro
        355                 360                 365

Leu Pro Val Val Lys Arg Lys Cys Thr Glu Glu Cys Glu Ile Asn Gly
370                 375                 380

Tyr Val Ile Pro Glu Gly Ala Leu Ile Leu Phe Asn Val Trp Gln Val
385                 390                 395                 400

```
Gly Arg Asp Pro Lys Tyr Trp Glu Lys Pro Leu Glu Phe Arg Pro Glu
                405                 410                 415

Arg Phe Leu Glu Asn Ala Ser Gln Gly Glu Gly Glu Ala Ala Ser Ile
            420                 425                 430

Asp Leu Arg Gly Gln His Phe Thr Leu Leu Pro Phe Gly Ser Gly Arg
        435                 440                 445

Arg Met Cys Pro Gly Val Asn Leu Ala Thr Ala Gly Met Ala Thr Leu
450                 455                 460

Leu Ser Ser Ile Ile Gln Cys Phe Asp Leu Gln Val Pro Gly Pro His
465                 470                 475                 480

Gly Gln Ile Leu Lys Gly Asp Val Lys Val Ser Met Asp Glu Arg
                485                 490                 495

Pro Gly Leu Thr Val Pro Arg Ala His Asn Leu Met Cys Val Pro Leu
                500                 505                 510

Ala Arg Ala Gly Val Ala Ala Lys Leu Leu Ser
            515                 520

<210> SEQ ID NO 5
<211> LENGTH: 519
<212> TYPE: PRT
<213> ORGANISM: Medicago truncatula

<400> SEQUENCE: 5

Met Glu Pro Leu Leu Ala Phe Thr Leu Phe Leu Ser Ser Leu Ile
1               5                   10                  15

Cys Tyr Ile Ile Phe Gln Pro Ile Leu Asn Arg Gln Lys Asn Leu Pro
                20                  25                  30

Pro Ser Pro Leu Phe Lys Leu Pro Ile Ile Gly His Met His Met Leu
            35                  40                  45

Gly Pro Leu Leu His His Ser Phe Asp Arg Leu Ser Gln Lys Tyr Gly
        50                  55                  60

Pro Ile Phe Ser Leu Asn Phe Gly Ser Val Leu Cys Val Val Ala Ser
65                  70                  75                  80

Thr Pro His Tyr Ala Lys Gln Ile Leu Gln Ile Asn Glu His Ala Phe
                85                  90                  95

Asn Cys Arg Asn Glu Ser Thr Ala Ile Lys Arg Leu Thr Tyr Glu Ala
                100                 105                 110

Ser Leu Ala Phe Ala Pro Tyr Gly Glu Tyr Trp Arg Phe Ile Lys Lys
            115                 120                 125

Leu Ser Met Asn Glu Leu Leu Gly Ser Arg Ser Ile Ser Ser Phe Gln
        130                 135                 140

His Leu Arg Leu Gln Glu Thr His Asn Leu Leu Lys Phe Phe Ala Asp
145                 150                 155                 160

Lys Ala Lys Asn Tyr Glu Ala Val Asn Val Thr Gln Glu Leu Leu Lys
                165                 170                 175

Leu Ser Asn Asn Val Ile Ser Lys Met Met Leu Gly Glu Ala Glu Glu
            180                 185                 190

Ala Arg Asp Val Val Arg Asp Val Thr Glu Ile Phe Gly Glu Phe Asn
        195                 200                 205

Val Ser Asp Phe Ile Trp Leu Phe Lys Lys Leu Asp Leu Gln Gly Phe
210                 215                 220

Gly Lys Arg Ile Glu Asp Leu Phe Met Arg Phe Asp Thr Leu Val Glu
225                 230                 235                 240

Arg Ile Ile Thr Lys Arg Glu Glu Leu Arg Lys Asn Lys Gly Arg Lys
                245                 250                 255
```

```
Glu Asn Lys Gly Glu Gln Gly Ala Glu Phe Arg Asp Phe Leu Asp Ile
            260                 265                 270

Leu Leu Asp Cys Ala Glu Asp Gln Asn Ser Glu Ile Lys Val Gln Arg
        275                 280                 285

Val His Ile Lys Ala Leu Ile Met Asp Phe Phe Thr Ala Gly Thr Asp
    290                 295                 300

Thr Thr Ser Ile Ser Thr Glu Trp Ala Leu Val Glu Leu Met Asn Asn
305                 310                 315                 320

Pro Ser Leu Leu Gln Lys Ala Arg Glu Glu Ile Asp Asn Ile Val Gly
                325                 330                 335

Lys Asn Arg Leu Val Asp Glu Ser Asp Gly Pro Asn Leu Pro Tyr Ile
            340                 345                 350

Gln Ala Ile Ile Lys Glu Thr Phe Arg Leu His Pro Pro Val Pro Met
        355                 360                 365

Val Thr Arg Arg Cys Val Thr Gln Cys Lys Ile Glu Asn Tyr Val Ile
    370                 375                 380

Pro Glu Asn Ser Leu Ile Phe Val Asn Asn Trp Ala Met Gly Arg Asn
385                 390                 395                 400

Pro Ala Tyr Trp Glu Lys Pro Leu Glu Phe Asn Pro Glu Arg Phe Leu
                405                 410                 415

Lys Asn Ser Ala Asn Ser Asn Gly Val Ile Asp Val Arg Gly Gln Asn
            420                 425                 430

Phe Gln Ile Leu Pro Phe Gly Ser Gly Arg Arg Met Cys Pro Gly Val
        435                 440                 445

Thr Leu Ala Met Gln Glu Val Pro Ala Leu Leu Gly Ala Ile Ile Gln
    450                 455                 460

Cys Phe Asp Phe Asn Phe Val Gly Pro Lys Gly Glu Ile Leu Lys Gly
465                 470                 475                 480

Arg Asp Ile Val Ile Asp Val Asn Glu Arg Pro Gly Leu Thr Ala Pro
                485                 490                 495

Arg Val His Asp Leu Val Cys Val Pro Val Glu Arg Ile Gly Cys Gly
            500                 505                 510

Gly Pro Leu Gln Ser Leu Gly
        515

<210> SEQ ID NO 6
<211> LENGTH: 1563
<212> TYPE: DNA
<213> ORGANISM: Medicago truncatula

<400> SEQUENCE: 6
atggaacctc tactattggc cttcacatta tttctttcat cactcatttg ctacataatt      60
ttccagccaa ttttaaaccg tcacaaaaac ctccctccat cgcctctatt caaacttccg     120
atcattggcc acatgcacat gttaggtccc cttctccacc actccttcga ccgcctctcc     180
caaaaatacg gaccaatatt ttcacttaac tttggttccg tcctctgcgt tgtttgcatcc    240 actcctcact acgcaaaaca aatccttcaa atcaacgaac acgcctttaa ttgtcgtaat     300
gaatcaactg caattaaacg cctcacctat gaagcatctc tagcttttgc accctatggc     360
gaatattgga gatttattaa aaaacttagt atgaatgagc ttttgggctc tcgtagcatt     420
agtagcttcc aacacttgcg tttacaagag actcacaacc tccttaagct tttcgctgat     480
aaagcgaaaa actacgaggc tgtgaatgtg acacaagagt tgctaaagtt gtcaaacaac     540
gtcatttcta aaatgatgtt gggggaagct gaggaggcta gggatgttgt gcgagatgtg     600
```

```
accgagattt ttggagagtt taatgtatcg gattttattt ggttgtttaa gaaacttgat    660
ttgcaagggt ttgggaagag gatagaggat ttgtttatga ggtttgatac attggtggaa    720
aggattatta gtaaaagaga agagttgagg aagaacaaag gaaggaaaga aaataagggt    780
gagcaaggtg ctgaattcag agactttctt gatatattgc ttgattgtgc cgaggatcaa    840
aattcagaaa taaagttca aagggttcac atcaaggcct tgattatgga tttctttaca    900
gcaggaacag acacaacatc aatttcaaca gaatgggcat tagttgagct aatgaacaac    960
ccttcattgt tacaaaaagc tcgtgaagaa atagacaatg tagtagggaa aaacagacta   1020
gtagatgaat ctgacggacc aaatcttcct tatattcaag ccataataaa agaaacattt   1080
cgtctacacc caccggttcc tatggtcact agaagatgtg tcacgcaatg caaaattgaa   1140
aattatgtga tcccagaaaa tagtttaatc tttgtgaata attgggctat gggaagaaac   1200
tcagcttatt gggacaaacc attggaattt aatccagaaa gatttctaaa aaattcaaca   1260
aattccaatg gggttattga tgtgaggggg caaaattttc agattttgcc atttgggtca   1320
ggaagaagga tgtgtcctgg ggttacttta gcaatgcaag aagttccagc tttgcttggt   1380
gccataattc aatgctttga ttttaatttt gtgggtccta aggtgagat  tttgaagggt   1440
ggtgatattg ttattgatgt gaatgaaagg ccaggattga ctgctcctag ggtgcatgat   1500
ttggtttgtg ttcctgttga aaggtttgct tgtggtggac ctcttcaaag ccttggatgt   1560
tga                                                                 1563

<210> SEQ ID NO 7
<211> LENGTH: 520
<212> TYPE: PRT
<213> ORGANISM: Medicago truncatula

<400> SEQUENCE: 7

Met Glu Pro Leu Leu Ala Phe Thr Leu Phe Leu Ser Ser Leu Ile
1               5                   10                  15

Cys Tyr Ile Ile Phe Gln Pro Ile Leu Asn Arg His Lys Asn Leu Pro
            20                  25                  30

Pro Ser Pro Leu Phe Lys Leu Pro Ile Ile Gly His Met His Met Leu
        35                  40                  45

Gly Pro Leu Leu His His Ser Phe Asp Arg Leu Ser Gln Lys Tyr Gly
    50                  55                  60

Pro Ile Phe Ser Leu Asn Phe Gly Ser Val Leu Cys Val Val Ala Ser
65                  70                  75                  80

Thr Pro His Tyr Ala Lys Gln Ile Leu Gln Ile Asn Glu His Ala Phe
                85                  90                  95

Asn Cys Arg Asn Glu Ser Thr Ala Ile Lys Arg Leu Thr Tyr Glu Ala
            100                 105                 110

Ser Leu Ala Phe Ala Pro Tyr Gly Glu Tyr Trp Arg Phe Ile Lys Lys
        115                 120                 125

Leu Ser Met Asn Glu Leu Leu Gly Ser Arg Ser Ile Ser Ser Phe Gln
    130                 135                 140

His Leu Arg Leu Gln Glu Thr His Asn Leu Leu Lys Leu Phe Ala Asp
145                 150                 155                 160

Lys Ala Lys Asn Tyr Glu Ala Val Asn Val Thr Gln Glu Leu Leu Lys
                165                 170                 175

Leu Ser Asn Asn Val Ile Ser Lys Met Met Leu Gly Glu Ala Glu Glu
            180                 185                 190
```

```
Ala Arg Asp Val Val Arg Asp Val Thr Glu Ile Phe Gly Glu Phe Asn
        195                 200                 205
Val Ser Asp Phe Ile Trp Leu Phe Lys Lys Leu Asp Leu Gln Gly Phe
    210                 215                 220
Gly Lys Arg Ile Glu Asp Leu Phe Met Arg Phe Asp Thr Leu Val Glu
225                 230                 235                 240
Arg Ile Ile Ser Lys Arg Glu Glu Leu Arg Lys Asn Lys Gly Arg Lys
                245                 250                 255
Glu Asn Lys Gly Glu Gln Gly Ala Glu Phe Arg Asp Phe Leu Asp Ile
            260                 265                 270
Leu Leu Asp Cys Ala Glu Asp Gln Asn Ser Glu Ile Lys Val Gln Arg
        275                 280                 285
Val His Ile Lys Ala Leu Ile Met Asp Phe Phe Thr Ala Gly Thr Asp
    290                 295                 300
Thr Thr Ser Ile Ser Thr Glu Trp Ala Leu Val Glu Leu Met Asn Asn
305                 310                 315                 320
Pro Ser Leu Leu Gln Lys Ala Arg Glu Glu Ile Asp Asn Val Val Gly
                325                 330                 335
Lys Asn Arg Leu Val Asp Glu Ser Asp Gly Pro Asn Leu Pro Tyr Ile
            340                 345                 350
Gln Ala Ile Ile Lys Glu Thr Phe Arg Leu His Pro Pro Val Pro Met
        355                 360                 365
Val Thr Arg Arg Cys Val Thr Gln Cys Lys Ile Glu Asn Tyr Val Ile
    370                 375                 380
Pro Glu Asn Ser Leu Ile Phe Val Asn Asn Trp Ala Met Gly Arg Asn
385                 390                 395                 400
Ser Ala Tyr Trp Asp Lys Pro Leu Glu Phe Asn Pro Glu Arg Phe Leu
                405                 410                 415
Lys Asn Ser Thr Asn Ser Asn Gly Val Ile Asp Val Arg Gly Gln Asn
            420                 425                 430
Phe Gln Ile Leu Pro Phe Gly Ser Gly Arg Arg Met Cys Pro Gly Val
        435                 440                 445
Thr Leu Ala Met Gln Glu Val Pro Ala Leu Leu Gly Ala Ile Ile Gln
    450                 455                 460
Cys Phe Asp Phe Asn Phe Val Gly Pro Lys Gly Glu Ile Leu Lys Gly
465                 470                 475                 480
Gly Asp Ile Val Ile Asp Val Asn Glu Arg Pro Gly Leu Thr Ala Pro
                485                 490                 495
Arg Val His Asp Leu Val Cys Val Pro Val Glu Arg Phe Ala Cys Gly
            500                 505                 510
Gly Pro Leu Gln Ser Leu Gly Cys
        515                 520
```

<210> SEQ ID NO 8
<211> LENGTH: 1488
<212> TYPE: DNA
<213> ORGANISM: Medicago truncatula

<400> SEQUENCE: 8

```
atgatttccc attccttctc attagctatg attttgctcc tatttctttt cattttttcag      60 cttctctctt acttaaagag aaacaagaag ttgcatgcac gattaccacc tcaccctcca     120
agtccaccag caataccaat aattggacat cttcatctcc tcaaaccact cattcatcag     180
gcctttcgcc acctctccga tcaatatggc cctttaatat cccttcgact tggctcctct     240
```

```
caatttatca ttgttaacac tccatcactc gccaaagagt ttctcaagac acatgagctc    300
acttattctc accgtaaaat gagcatagcc atcaacgtag ttgcctatga tgatgcaact    360
tttgctttcg ctccttatgg gacttattgg aaatttatta aaaagctcag caccactgag    420
ctcttgggta atcgaaccat ggcacaattt ctaccgattc gaacccaaga actccatgaa    480
ttcattcaaa ctttggcaaa taagtctaag gcagaagaaa gtgtgaacct cacacaagct    540
ttgataaagc tttccaacaa cataatatca cggatgatgt tgagtattga ttgctcagga    600
acagataacc aagcagaaca agttagggct ttggttcgcg aggtaacaca gattttggga    660
gaatttaatg tttcagattt tataggaatt tcaagaact  ttgacttgca agggtttaaa    720
aaggagggcc ttggacatac acaaaaggta gatgctttgt tggataagat tatttctgat    780
cgtgaagaac taagaaggga agccaagcta atagatggtg gtggtgagaa tggtgaagaa    840
gagagactga agattttct tgacatttgt ctagatgtct acagtgagaa aaactgtgaa    900 gtcaactta ctagaaatca tatcaaatca ttaatattgg attctttacg gcagcaaccg    960
acactactgc catctccgtg gaatgggcaa tatcagaact gtttaacaat ccaagggtgc   1020
ggaaaaaagc acaagaggag gtggataaag ttactagaaa ggaaagactt gtgtgtgaag   1080
aagacggtcc aaaccttcct tatatacatg ctatcacaaa agaaaatgag gcttcatccc   1140
ccgataccga tgattatgag gaagggaatg gaagattgtg tggttgatgg taacatgatt   1200
ctgaaaggct caatggtttg tgtaaacatt gggctatgg caagggaccc aaagatatgg   1260
gaaaacccat tagagtttag gccagaaagg ttttttagaaa acaaagatat tgacatgaaa   1320
gggcaccagt ttgagttgtt gccatttggt tctggaagga gaggttgtcc tggtatgcct   1380
ttggccctac gtcaattacc cactgtaatt ggtgctttgg tacaatgctt tgagtggaag   1440
atgcttgatt cggaatgtaa gatcttagat caaggcaaaa aaaattga                1488

<210> SEQ ID NO 9
<211> LENGTH: 495
<212> TYPE: PRT
<213> ORGANISM: Medicago truncatula

<400> SEQUENCE: 9

Met Ile Ser His Ser Phe Ser Leu Ala Met Ile Leu Leu Leu Phe Leu
1               5                   10                  15

Phe Ile Phe Gln Leu Leu Ser Tyr Leu Lys Arg Asn Lys Lys Leu His
            20                  25                  30

Ala Arg Leu Pro Pro His Pro Ser Pro Pro Ala Ile Pro Ile Ile
        35                  40                  45

Gly His Leu His Leu Leu Lys Pro Leu Ile His Gln Ala Phe Arg His
    50                  55                  60

Leu Ser Asp Gln Tyr Gly Pro Leu Ile Ser Arg Leu Gly Ser Ser
65                  70                  75                  80

Gln Phe Ile Ile Val Asn Thr Pro Ser Leu Ala Lys Glu Phe Leu Lys
                85                  90                  95

Thr His Glu Leu Thr Tyr Ser His Arg Lys Met Ser Ile Ala Ile Asn
            100                 105                 110

Val Val Ala Tyr Asp Asp Ala Thr Phe Ala Phe Ala Pro Tyr Gly Thr
        115                 120                 125

Tyr Trp Lys Phe Ile Lys Lys Leu Ser Thr Thr Glu Leu Leu Gly Asn
    130                 135                 140

Arg Thr Met Ala Gln Phe Leu Pro Ile Arg Thr Gln Glu Leu His Glu
145                 150                 155                 160
```

```
Phe Ile Gln Thr Leu Ala Asn Lys Ser Lys Ala Glu Glu Ser Val Asn
                165                 170                 175
Leu Thr Gln Ala Leu Ile Lys Leu Ser Asn Asn Ile Ile Ser Arg Met
            180                 185                 190
Met Leu Ser Ile Asp Cys Ser Gly Thr Asp Asn Gln Ala Glu Gln Val
        195                 200                 205
Arg Ala Leu Val Arg Glu Val Thr Gln Ile Phe Gly Glu Phe Asn Val
    210                 215                 220
Ser Asp Phe Ile Gly Ile Phe Lys Asn Phe Asp Leu Gln Gly Phe Lys
225                 230                 235                 240
Lys Glu Gly Leu Gly His Thr Gln Lys Val Asp Ala Leu Leu Asp Lys
                245                 250                 255
Ile Ile Ser Asp Arg Glu Glu Leu Arg Arg Glu Ala Lys Leu Ile Asp
            260                 265                 270
Gly Gly Gly Glu Asn Gly Glu Glu Arg Leu Lys Asp Phe Leu Asp
        275                 280                 285
Ile Cys Leu Asp Val Tyr Ser Glu Lys Asn Cys Glu Val Asn Phe Thr
    290                 295                 300
Arg Asn His Ile Lys Ser Leu Ile Leu Asp Ser Leu Arg Gln Gln Pro
305                 310                 315                 320
Thr Leu Leu Pro Ser Pro Trp Asn Gly Gln Tyr Gln Asn Cys Leu Thr
                325                 330                 335
Ile Gln Gly Cys Gly Lys Lys His Lys Arg Arg Trp Ile Lys Leu Leu
            340                 345                 350
Glu Arg Lys Asp Leu Cys Val Lys Lys Thr Val Gln Thr Phe Leu Ile
        355                 360                 365
Tyr Met Leu Ser Gln Lys Lys Met Arg Leu His Pro Pro Ile Pro Met
    370                 375                 380
Ile Met Arg Lys Gly Met Glu Asp Cys Val Val Asp Gly Asn Met Ile
385                 390                 395                 400
Leu Lys Gly Ser Met Val Cys Val Asn Ile Trp Ala Met Ala Arg Asp
                405                 410                 415
Pro Lys Ile Trp Glu Asn Pro Leu Glu Phe Arg Pro Gly Arg Phe Leu
            420                 425                 430
Glu Asn Lys Asp Ile Asp Met Lys Gly His Gln Phe Glu Leu Leu Pro
        435                 440                 445
Phe Gly Ser Gly Arg Arg Gly Cys Pro Gly Met Pro Leu Ala Leu Arg
    450                 455                 460
Gln Leu Pro Thr Val Ile Gly Ala Leu Val Gln Cys Phe Glu Trp Lys
465                 470                 475                 480
Met Leu Asp Ser Glu Cys Lys Ile Leu Asp Gln Gly Lys Lys Asn
                485                 490                 495

<210> SEQ ID NO 10
<211> LENGTH: 954
<212> TYPE: DNA
<213> ORGANISM: Medicago truncatula

<400> SEQUENCE: 10
atggtggtag atccggtagt tattccaaag ttgaggatgg atgaacaaag agctattcaa      60
gaagctgctt ctgctggatt gaaaagtatg gagcaactaa ttcgtgtgct tcttctcaa     120 acttcttctt cttcttcttc ttcaaatcaa cttaaccaac tagatctggt caataaactt     180
gattgtactg aaattactga tttcactgtt tctaagttta aacggttat taacttgtta      240
```

-continued

```
aatcgaaccg gtcacgctcg ttttcgtcgt gcaccttctt ctcctccttg ttcttcttat    300
caatttcaat ctcaatctca acctgagaaa ttcaagactc aaccacagtc aactactctt    360
gattttgcaa aaccgattca attagttaag tcaaatccaa atcccaatct caaacctaaa    420
actaatcaat ctactgattt atctgtttct caatactcca atcaaagga agcttatagc     480
atctctacca ctacttcttc tttcatgtcc accatcaccg agatggaag cgtttccgac     540
ggtaaaatag gtcctatcat ttcctctggc aagcctcctc tagcttcatc tcaccggaaa    600
aggtgtcacg aagccacaat ctctggcaaa gtctcatcct ccggtcactg ccattgctcc    660
aagagaagga aatctcgtgt gaagagaaca attcgtgttc cggcgataag ttcaaaggtc    720
gctgatatac catcagacga attttcgtgg aggaaatacg gtcaaaaacc tattaaaggt    780
tcaccttacc cacgtggtta ctacaagtgc agtagcttca aaggatgtcc ggcgaggaag    840
catgtagaaa gagcacaaga cgatcccaat atgcttgttg ttacttacga gggagagcac    900
cgtcacgcac aaaccgtcgt aactggcgcc ggattcatat ctcagcctct ttga          954
```

<210> SEQ ID NO 11
<211> LENGTH: 317
<212> TYPE: PRT
<213> ORGANISM: Medicago truncatula

<400> SEQUENCE: 11

```
Met Val Val Asp Pro Val Ile Pro Lys Leu Arg Met Asp Glu Gln
1               5                   10                  15

Arg Ala Ile Gln Glu Ala Ala Ser Ala Gly Leu Lys Ser Met Glu Gln
            20                  25                  30

Leu Ile Arg Val Leu Ser Ser Gln Thr Ser Ser Ser Ser Ser Ser Ser
        35                  40                  45

Asn Gln Leu Asn Gln Leu Asp Leu Val Asn Lys Leu Asp Cys Thr Glu
    50                  55                  60

Ile Thr Asp Phe Thr Val Ser Lys Phe Lys Thr Val Ile Asn Leu Leu
65                  70                  75                  80

Asn Arg Thr Gly His Ala Arg Phe Arg Arg Ala Pro Ser Ser Pro
                85                  90                  95

Cys Ser Ser Tyr Gln Phe Gln Ser Gln Ser Gln Pro Glu Lys Phe Lys
            100                 105                 110

Thr Gln Pro Gln Ser Thr Thr Leu Asp Phe Ala Lys Pro Ile Gln Leu
        115                 120                 125

Val Lys Ser Asn Pro Asn Pro Asn Leu Lys Pro Lys Thr Asn Gln Ser
    130                 135                 140

Thr Asp Leu Ser Val Ser Gln Tyr Ser Lys Ser Lys Glu Ala Tyr Ser
145                 150                 155                 160

Ile Ser Thr Thr Thr Ser Ser Phe Met Ser Thr Ile Thr Gly Asp Gly
                165                 170                 175

Ser Val Ser Asp Gly Lys Ile Gly Pro Ile Ser Ser Gly Lys Pro
            180                 185                 190

Pro Leu Ala Ser Ser His Arg Lys Arg Cys His Glu Ala Thr Ile Ser
        195                 200                 205

Gly Lys Val Ser Ser Ser Gly His Cys His Cys Ser Lys Arg Arg Lys
    210                 215                 220

Ser Arg Val Lys Arg Thr Ile Arg Val Pro Ala Ile Ser Ser Lys Val
225                 230                 235                 240

Ala Asp Ile Pro Ser Asp Glu Phe Ser Trp Arg Lys Tyr Gly Gln Lys
```

```
                        245                 250                 255
Pro Ile Lys Gly Ser Pro Tyr Pro Arg Gly Tyr Tyr Lys Cys Ser Ser
            260                 265                 270

Phe Lys Gly Cys Pro Ala Arg Lys His Val Glu Arg Ala Gln Asp Asp
        275                 280                 285

Pro Asn Met Leu Val Val Thr Tyr Glu Gly Glu His Arg His Ala Gln
    290                 295                 300

Thr Val Val Thr Gly Ala Gly Phe Ile Ser Gln Pro Leu
305                 310                 315

<210> SEQ ID NO 12
<211> LENGTH: 25
<212> TYPE: DNA
<213> ORGANISM: Artificial Sequence
<220> FEATURE:
<223> OTHER INFORMATION: Synthetic primer

<400> SEQUENCE: 12
ccacgacacc atcctaaatt gtatc                                           25

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
tggtgtgact aatgcctttt tgac                                            24

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
gcaacgcaaa cggaatagtg t                                               21

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
tggtcctctg cttgcacctt                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
cacgctgttt ccctgatct                                                  20

<210> SEQ ID NO 17
<211> LENGTH: 21
<212> TYPE: DNA
<213> ORGANISM: Artificial Sequence
```

<220> FEATURE:
<223> OTHER INFORMATION: Synthetic primer

<400> SEQUENCE: 17
tcaacaacgc cggtaatctt g    21

<210> SEQ ID NO 18
<211> LENGTH: 22
<212> TYPE: DNA
<213> ORGANISM: Artificial Sequence
<220> FEATURE:
<223> OTHER INFORMATION: Synthetic primer

<400> SEQUENCE: 18
gtgaaggagg tattccgttt gc    22

<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
tctcacactc ttcggtgcat tt    22

<210> SEQ ID NO 20
<211> LENGTH: 23
<212> TYPE: DNA
<213> ORGANISM: Artificial Sequence
<220> FEATURE:
<223> OTHER INFORMATION: Synthetic primer

<400> SEQUENCE: 20
cagcaggaac agacacaaca tca    23

<210> SEQ ID NO 21
<211> LENGTH: 24
<212> TYPE: DNA
<213> ORGANISM: Artificial Sequence
<220> FEATURE:
<223> OTHER INFORMATION: Synthetic primer

<400> SEQUENCE: 21
tgaagggttg ttcattagct caac    24

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
ttggtggtcg ttttgtttgc    20

<210> SEQ ID NO 23
<211> LENGTH: 25
<212> TYPE: DNA
<213> ORGANISM: Artificial Sequence
<220> FEATURE:
<223> OTHER INFORMATION: Synthetic primer

<400> SEQUENCE: 23
ccctaatacc aaaacaagag ctttc    25